US010799398B2

(12) United States Patent
Eimann et al.

(10) Patent No.: US 10,799,398 B2
(45) Date of Patent: Oct. 13, 2020

(54) PROCESS AND APPARATUS FOR MANUFACTURING AN ABSORBENT ARTICLE USING A LASER SOURCE

(71) Applicant: The Procter & Gamble Company, Cincinnati, OH (US)

(72) Inventors: Klaus Eimann, Zellingen (DE); Bradley Edward Walsh, Cincinnati, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 753 days.

(21) Appl. No.: 15/158,656

(22) Filed: May 19, 2016

(65) Prior Publication Data

US 2016/0354254 A1    Dec. 8, 2016

Related U.S. Application Data

(60) Provisional application No. 62/169,578, filed on Jun. 2, 2015.

(51) Int. Cl.
*A61F 13/15*    (2006.01)
*B23K 26/06*    (2014.01)
(Continued)

(52) U.S. Cl.
CPC .. *A61F 13/15593* (2013.01); *A61F 13/15577* (2013.01); *A61F 13/15723* (2013.01); *A61F 13/15739* (2013.01); *A61F 13/15764* (2013.01); *B23K 26/0604* (2013.01); *B23K 26/083* (2013.01); *B23K 26/38* (2013.01); *B23K 26/402* (2013.01); *B23K 2103/172* (2018.08); *B23K 2103/50* (2018.08)

(58) Field of Classification Search
CPC .......... A61F 13/15723; A61F 13/15593; A61F 13/15739; A61F 3/15756; A61F 3/15764; B23K 26/0604; B23K 26/359
See application file for complete search history.

(56) References Cited

U.S. PATENT DOCUMENTS 3,848,594 A    11/1974  Buell
3,860,003 A    1/1975   Buell
(Continued)

FOREIGN PATENT DOCUMENTS

WO    WO 2017/105889 A1    6/2017

*Primary Examiner* — Michael H. Wilson
*Assistant Examiner* — Taryn Trace Willett
(74) *Attorney, Agent, or Firm* — C. Brant Cook

(57) ABSTRACT

The present disclosure relates to methods and apparatuses for imparting a first line of weakness and a second line of weakness into one or more layers of an advancing substrate, such as a belt assembly. The first line of weakness is coincident with the second line of weakness. The advancing substrate may be a belt assembly including an outer layer, an inner layer, and one or more elastic strands disposed between the outer layer and the inner layer. A first surface of the belt assembly may be acted on by a first laser beam that operatively engages a first scan head and a second surface of the belt assembly may be acted on by a second laser beam that operatively engages a second scan head. A trim removal member may be used to separate the first and second lines of weakness forming a trim portion and a separation edge.

34 Claims, 26 Drawing Sheets

(51) Int. Cl.
*B23K 26/08* (2014.01)
*B23K 26/38* (2014.01)
*B23K 26/402* (2014.01)
*B23K 103/16* (2006.01)
*B23K 103/00* (2006.01)

(56) References Cited

U.S. PATENT DOCUMENTS

| | | |
|---|---|---|
| 4,116,892 A | 9/1978 | Schwarz |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,946,527 A | 8/1990 | Battrell |
| 5,151,092 A | 9/1992 | Buell et al. |
| 5,167,897 A | 12/1992 | Weber et al. |
| 5,221,274 A | 6/1993 | Buell et al. |
| 5,360,420 A | 11/1994 | Cook et al. |
| 5,562,646 A | 10/1996 | Goldman et al. |
| 5,599,335 A | 2/1997 | Goldman et al. |
| 5,622,581 A * | 4/1997 | Ducker ............ A61F 13/15593 156/163 |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,916,661 A | 6/1999 | Benson et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,153,209 A | 11/2000 | Vega et al. |
| 6,410,129 B2 | 6/2002 | Zhang et al. |
| 6,426,444 B2 | 7/2002 | Roe et al. |
| 6,500,377 B1 | 12/2002 | Schneider et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,743,321 B2 * | 6/2004 | Guralski ............ A61F 13/15593 156/204 |
| 6,790,798 B1 | 9/2004 | Suzuki et al. |
| 6,825,393 B2 | 11/2004 | Roe et al. |
| 6,838,040 B2 * | 1/2005 | Mlinar ................ B26F 3/002 225/2 |
| 6,861,571 B1 | 3/2005 | Roe et al. |
| 7,431,791 B2 * | 10/2008 | Heller ............ A61F 13/15723 156/253 |
| 7,569,039 B2 | 8/2009 | Matsuda et al. |
| 8,440,043 B1 | 5/2013 | Schneider et al. |
| 8,820,513 B2 | 9/2014 | Papsdorf et al. |
| 9,387,131 B2 * | 7/2016 | Andrews ................ A61F 13/15 |
| 2001/0014798 A1 * | 8/2001 | Fernfors ............ A61F 13/15723 604/390 |
| 2002/0103468 A1 * | 8/2002 | Nakakado ......... A61F 13/15601 604/358 |
| 2002/0148557 A1 * | 10/2002 | Heller ............... A61F 13/15723 156/252 |
| 2002/0157778 A1 * | 10/2002 | Sorenson .......... A61F 13/15593 156/264 |
| 2003/0051805 A1 * | 3/2003 | Mlinar .............. A61F 13/15756 156/269 |
| 2004/0035521 A1 * | 2/2004 | Nakakado ......... A61F 13/15593 156/229 |
| 2004/0060648 A1 * | 4/2004 | Thorson ............ A61F 13/15699 156/258 |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2005/0145322 A1 * | 7/2005 | Hoffman ........... A61F 13/15593 156/160 |
| 2007/0044608 A1 * | 3/2007 | Franke .............. A61F 13/15682 83/39 |
| 2008/0070378 A1 * | 3/2008 | Yeo .................... B23K 26/0604 438/460 |
| 2009/0312730 A1 | 12/2009 | LaVon et al. |
| 2009/0324905 A1 * | 12/2009 | Welch .............. A61F 13/15593 428/198 |
| 2010/0154992 A1 * | 6/2010 | Feinstein ............ B32B 38/0004 156/711 |
| 2011/0125125 A1 * | 5/2011 | Schneider ............. A61F 13/551 604/385.23 |
| 2012/0061015 A1 | 3/2012 | LaVon et al. |
| 2012/0061016 A1 | 3/2012 | LaVon et al. |
| 2012/0079926 A1 | 4/2012 | Long et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 * | 10/2013 | Schneider ......... A61F 13/15593 156/161 |
| 2013/0255865 A1 | 10/2013 | Brown et al. |
| 2014/0110037 A1 * | 4/2014 | Verboomen ....... A61F 13/15747 156/66 |
| 2014/0155855 A1 * | 6/2014 | Romzek ............ A61F 13/15577 604/385.11 |
| 2014/0171895 A1 * | 6/2014 | Thomas ............ A61F 13/49012 604/385.3 |
| 2016/0128877 A1 * | 5/2016 | Chandrasekaran ........ C09J 7/29 24/306 |
| 2017/0189999 A1 * | 7/2017 | Bookbinder ......... B23K 26/402 |

\* cited by examiner

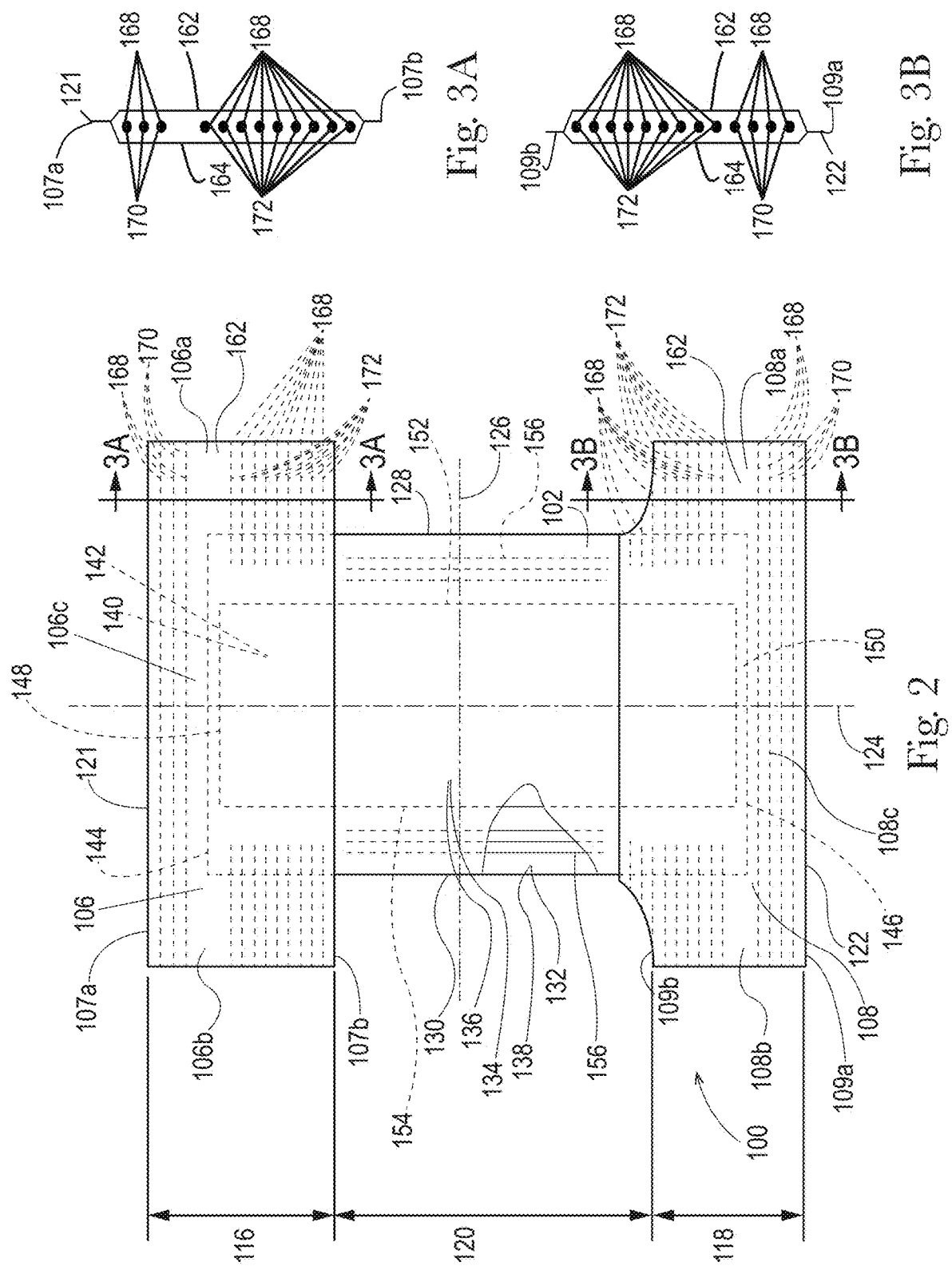

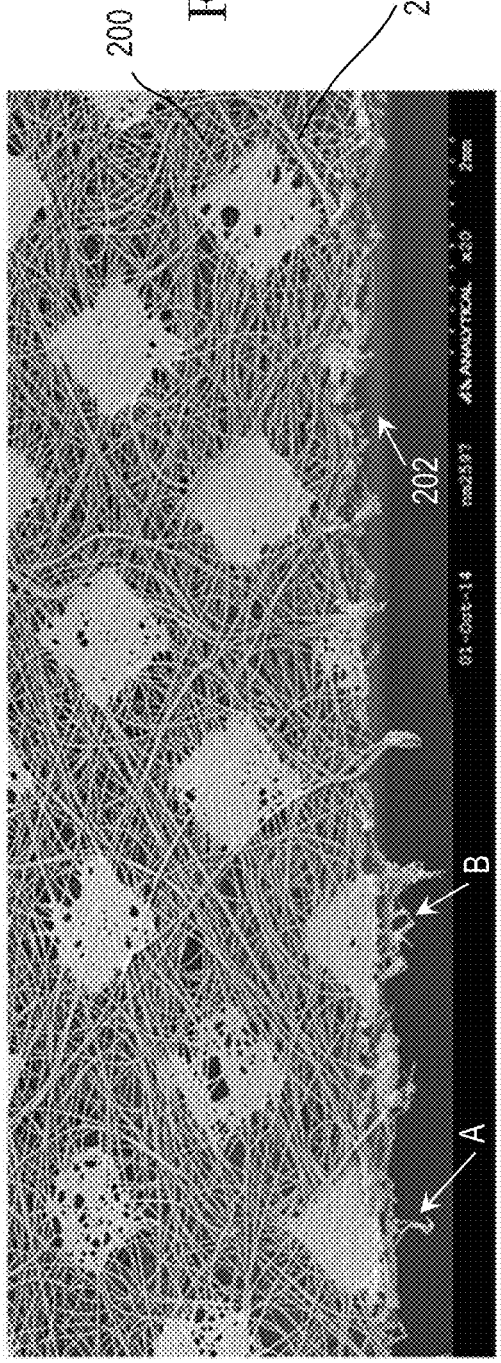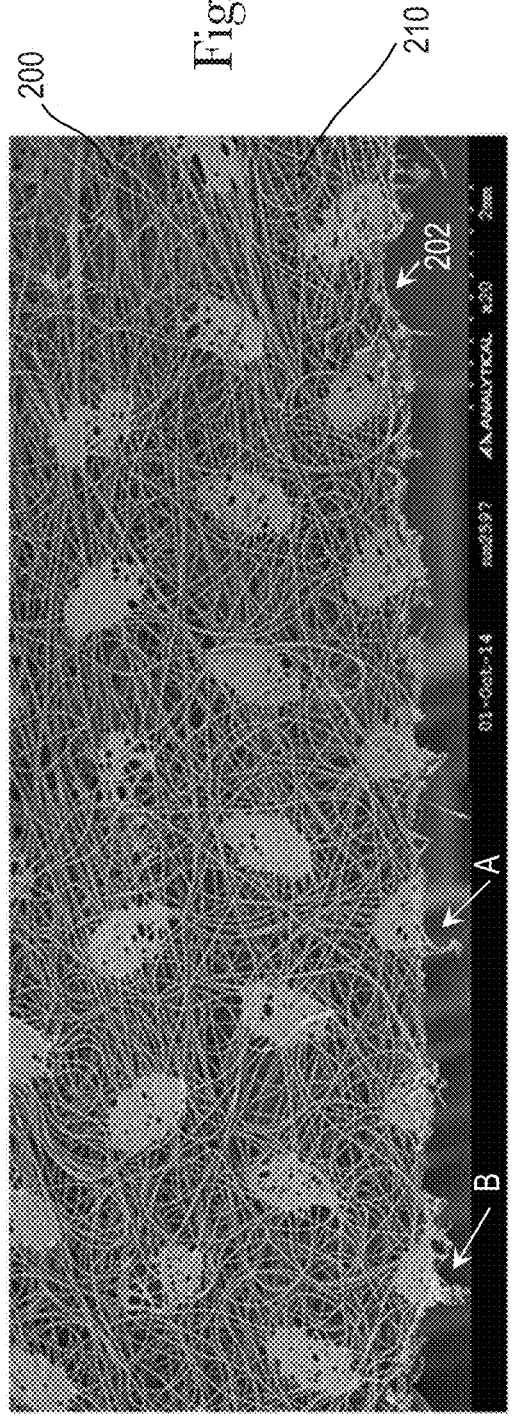

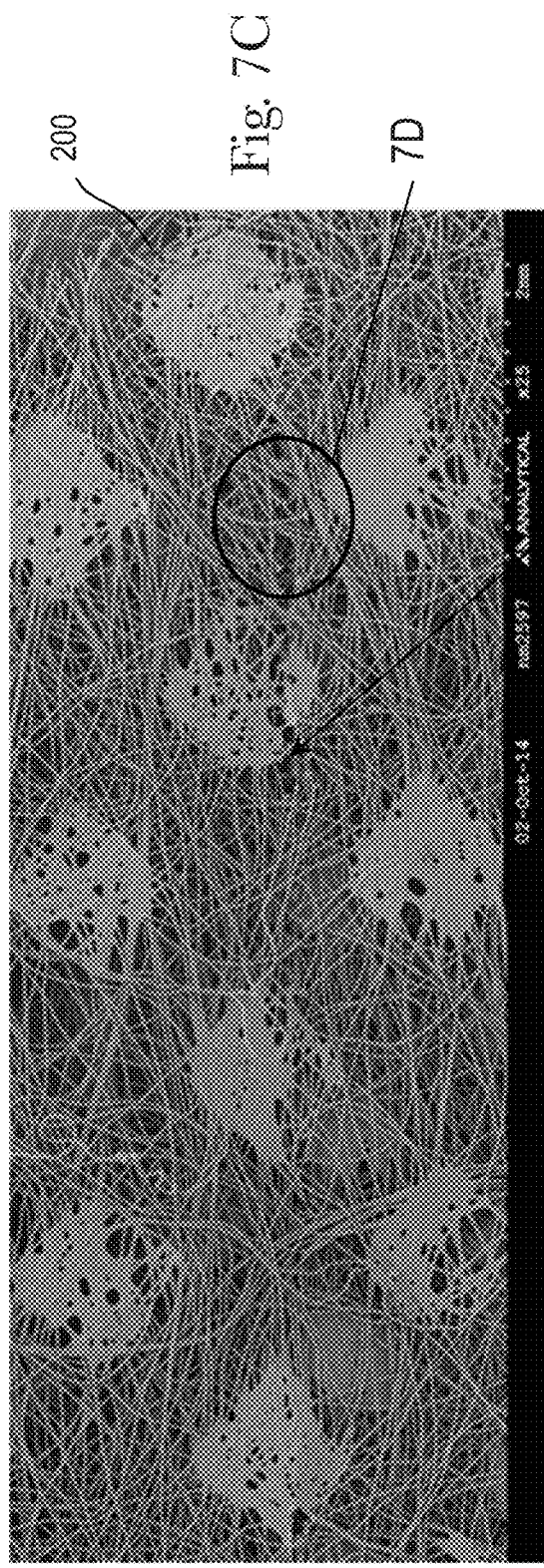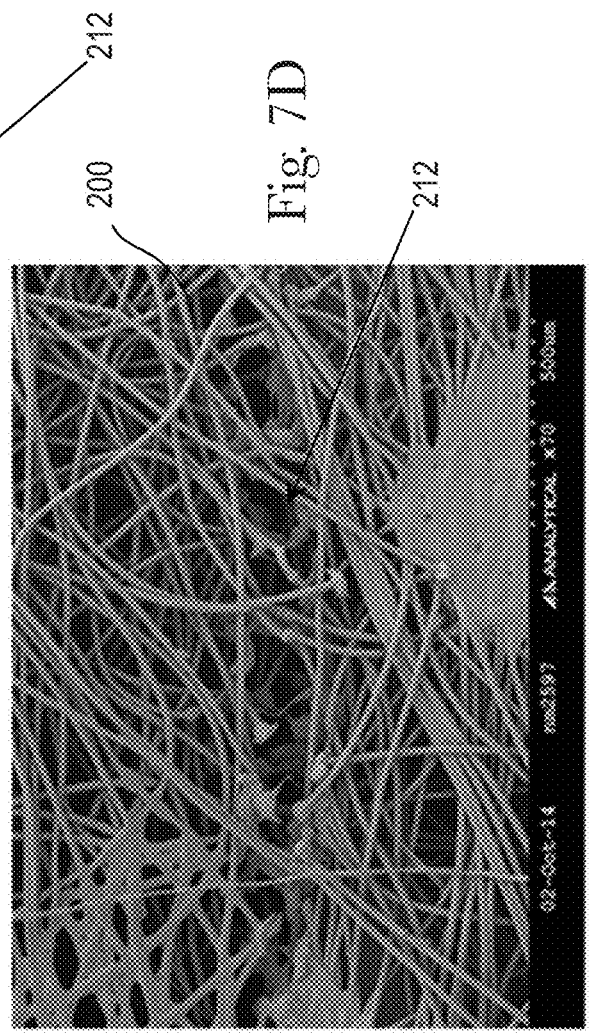

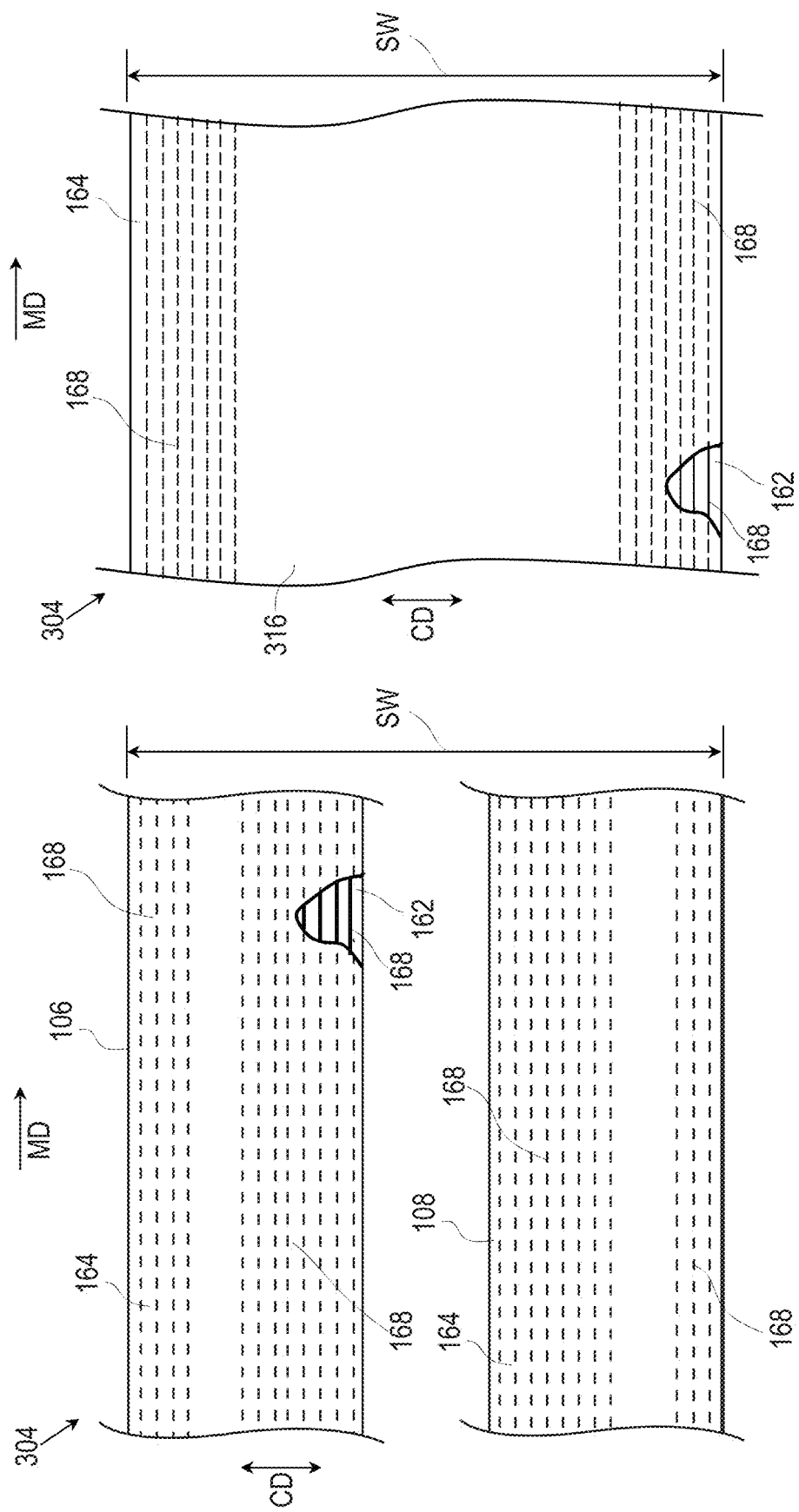

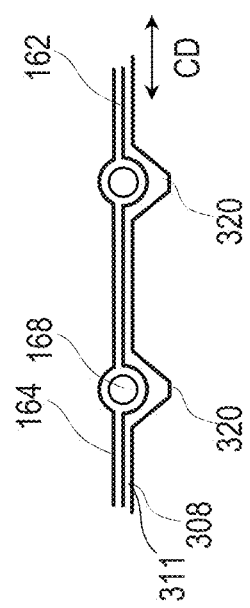
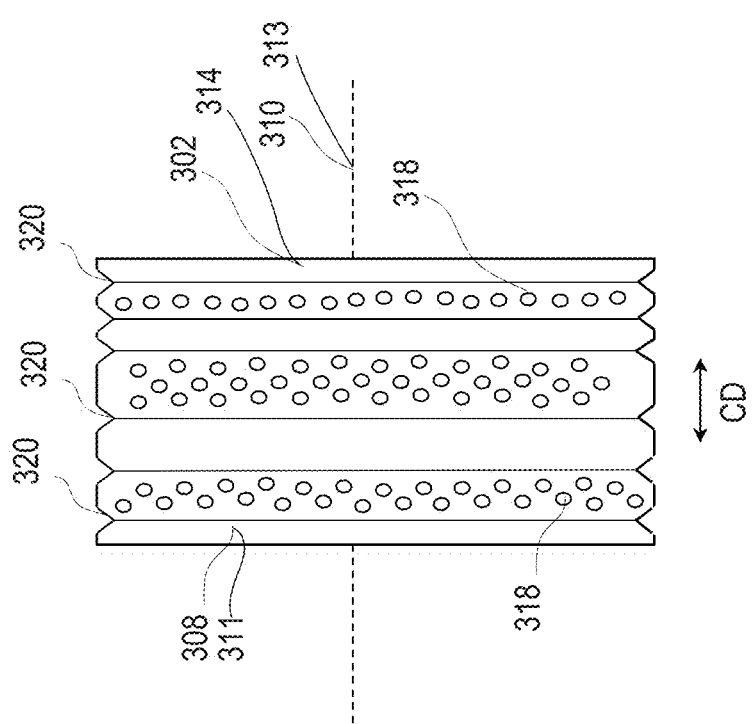

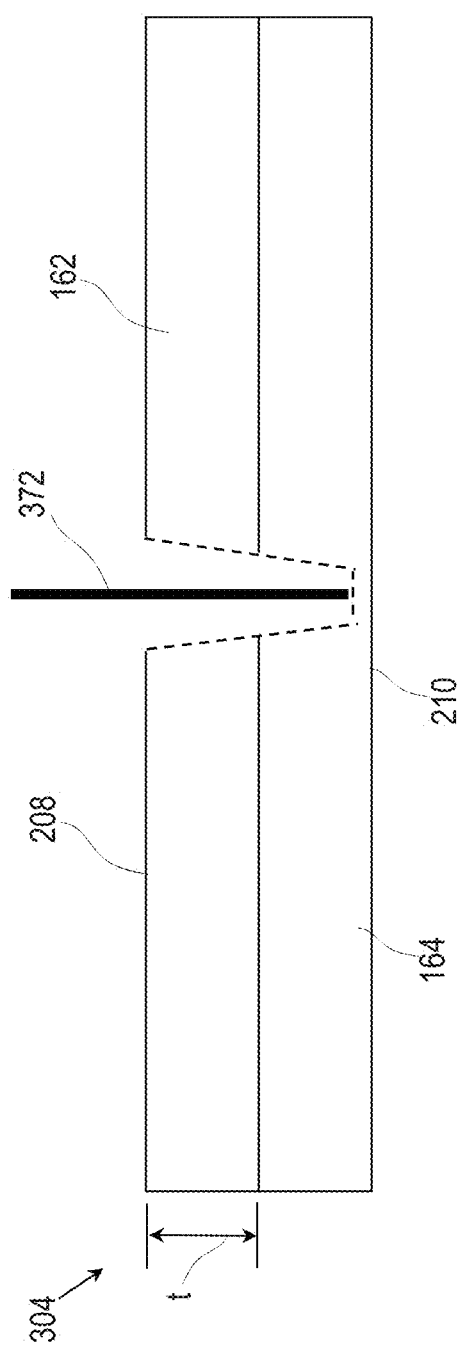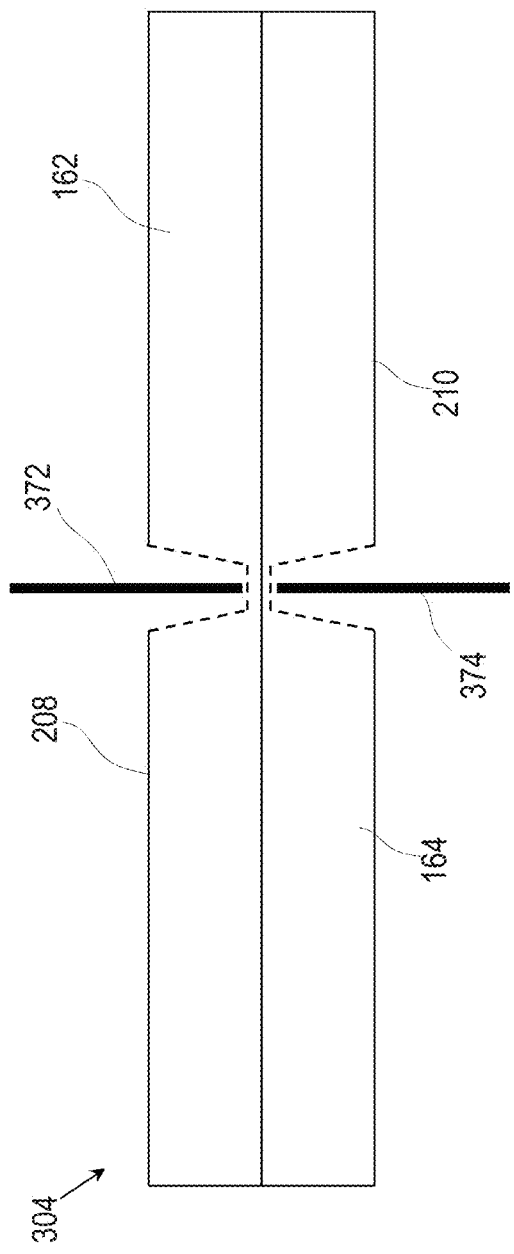

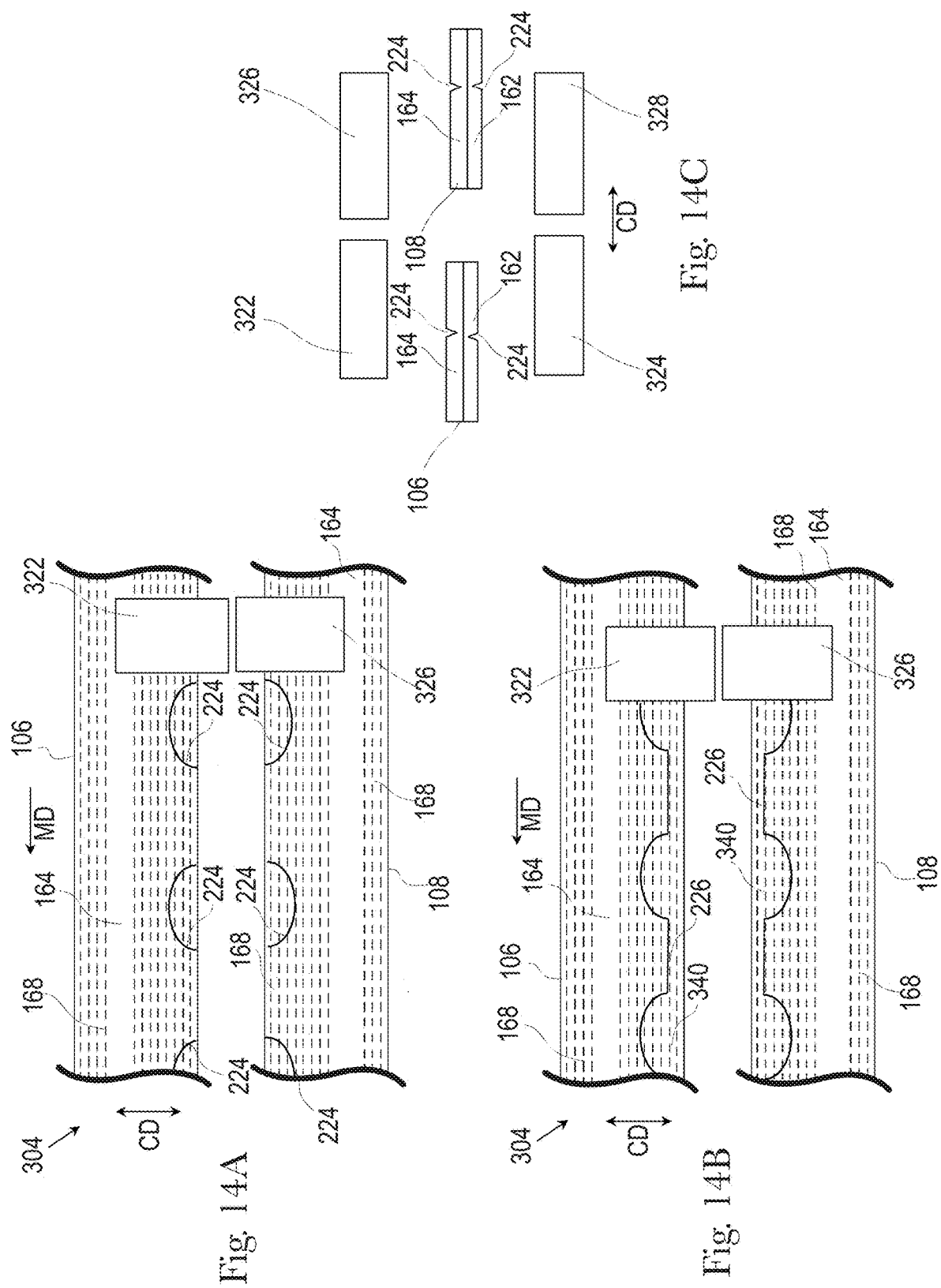

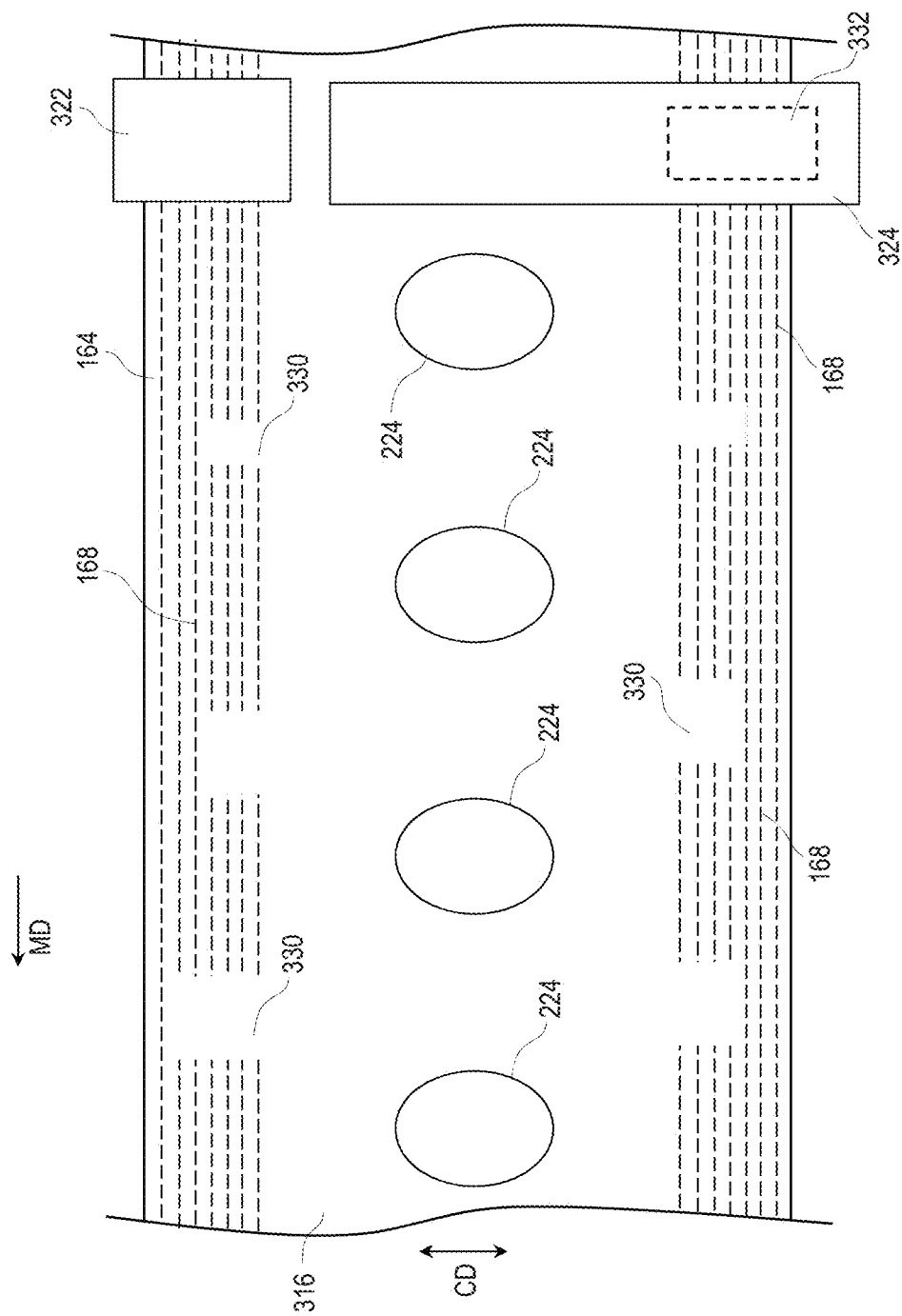

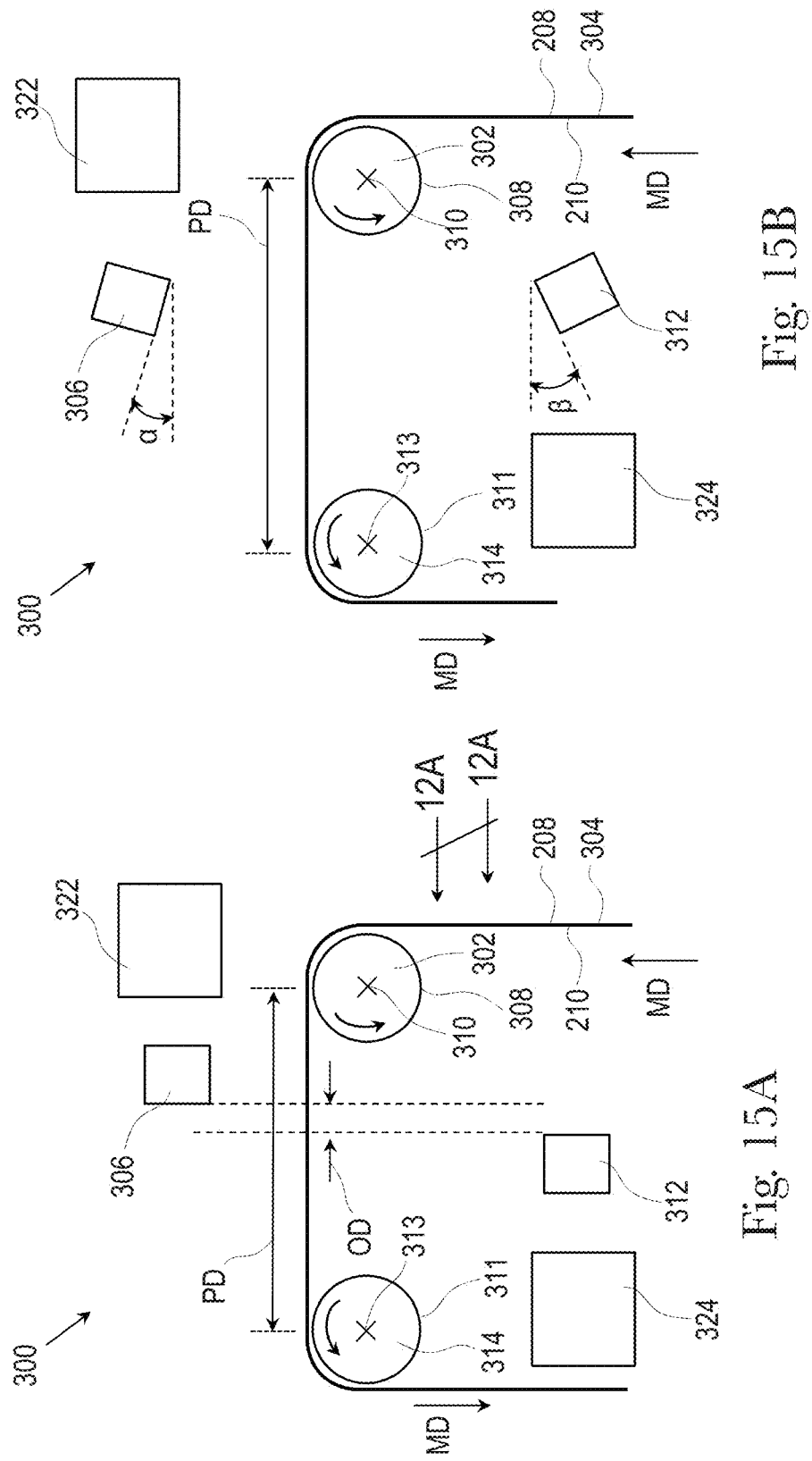

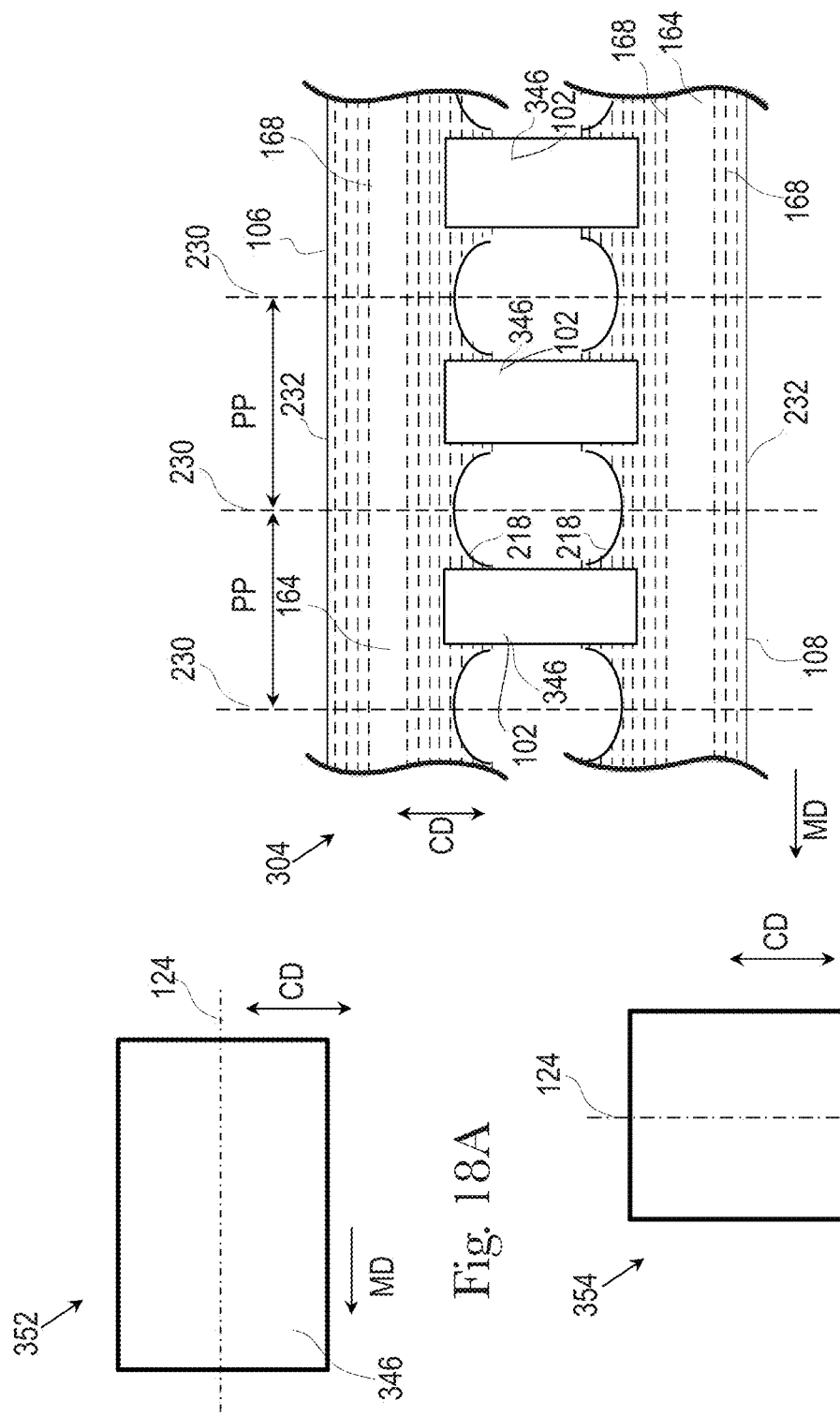

PROCESS AND APPARATUS FOR MANUFACTURING AN ABSORBENT ARTICLE USING A LASER SOURCE

CROSS REFERENCE TO RELATED APPLICATION

This application claims the benefit of U.S. Provisional Application No. 62/169,578, filed Jun. 2, 2015, the substance of which is incorporated herein by reference.

FIELD OF THE INVENTION

The present disclosure relates to apparatuses and methods for manufacturing absorbent articles, and more particularly, methods and apparatuses for manufacturing absorbent articles using one or more laser sources to create a first line of weakness and a second line of weakness such that the first line of weakness is coincident with the second line of weakness.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to the advancing web and/or otherwise modify the advancing web. For example, some production operations are configured to construct elastic laminates including elastics bonded with the one or more substrates advancing in a machine direction. The operations may be further configured to cut and/or otherwise deactivate discrete lengths of the elastics. In some operations, an elastic laminate may advance through a cutting station that cuts the elastic in the advancing laminate. However, some current configurations have certain drawbacks. For example, some present cutting apparatuses may cause unintended damage to the elastic laminate, such as by severing the substrate while cutting the elastic. In addition, the blades on some current cutting apparatuses may be susceptible to wear after relatively short operating periods. Such blade wear may manifest itself in inconsistent elastic cutting. Further, a blade may be re-sharpened only a certain number of times before the cutting device, as a whole, needs to be replaced, and there are costs associated with maintaining worn cutting devices and ultimately replacing the cutting device. Further still, each time the shape of a cut needs to be changed, new blades having the desired shape need to be purchased for the cutting apparatus. Thus, it may be relatively expensive to maintain and replace cutting devices.

Similar to the above, other production operations are configured to advance substrates in a machine direction and cut and/or remove trim from the advancing substrates. In some operations, a substrate may advance through a cutting station that cuts trim from the advancing substrate. The trim may subsequently be diverted from the advancing substrate and into a vacuum chute or other similar apparatus for disposal. In some instances after passing through the cutting nip, the trim may remain attached to the advancing substrate by uncut fibers after passing through the cutting station. As such, the trim may undesirably continue to advance with the substrate along the assembly line negatively affecting further processing Consequently, it would be beneficial to provide methods and apparatuses that are configured to provide relatively consistent cutting of substrates and/or elastics without excessive and/or unintentional damage to the substrate, and that are configured to accurately remove trim from the advancing substrates. It would also be beneficial to provide methods and apparatuses that are not susceptible to blade wear.

SUMMARY OF THE INVENTION

The present disclosure relates to methods and apparatuses for assembling absorbent articles, and more particularly, methods and apparatuses for using a laser source to cut and/or impart one or more lines of weakness. In some embodiments, a method for manufacturing an absorbent article includes the steps of: advancing a belt assembly, wherein the belt assembly comprises a first surface and a second surface; and advancing the belt assembly to a first laser assembly, where the first laser assembly comprises a first laser source positioned adjacent the first surface and a second laser source positioned adjacent the second surface, wherein the first laser source operatively engages the first surface of the belt assembly imparting a first line of weakness on the first surface of the belt assembly and the second laser source operatively engages that second surface of the belt assembly imparting a second line of weakness on the second surface of the belt assembly, wherein the first line of weakness and the second line of weakness are coincident.

In some embodiments, a method for manufacturing an absorbent article includes the steps of: rotating a first guide roller about a first axis of rotation; rotating a second guide roller about a second axis of rotation, wherein the first guide roller is adjacent the second guide roller; advancing a belt assembly around a portion of the first guide roller, wherein the belt assembly comprises a first substrate and a second substrate; disposing the second substrate of the belt assembly on an outer circumferential surface of the first guide roll; advancing the belt assembly to a first laser beam, wherein the first laser beam imparts a first line of weakness into the first substrate; advancing the substrate assembly between the first guide roller and the second guide roller; disposing the first substrate of the belt assembly on an outer circumferential surface of the second guide roll; and advancing the belt assembly to a second laser beam, wherein the second laser beam imparts a second line of weakness into the second substrate, wherein the second line of weakness is coincident with the first line of weakness.

In some embodiments, a method for manufacturing an absorbent article includes the steps of: advancing a belt assembly around a portion of a first guide roller, wherein the belt assembly comprises a first surface and a second surface; advancing the belt assembly around a portion of a second guide roller, wherein an unsupported portion of the belt assembly is suspended between the first guide roller and the second guide roller; imparting a first line of weakness into the first surface of the belt assembly using a first laser beam, wherein the first laser beam acts on the unsupported portion of the belt assembly between the first guide roller and the second guide roller; imparting a second line of weakness into the second surface of the belt assembly using a second laser beam, wherein the second laser beam acts on the unsupported portion of the belt assembly between the first guide roller and the second guide roller; and wherein the first line of weakness is coincident with the second line of weakness.

In some embodiments, a method for manufacturing an absorbent article includes the steps of: advancing an absorbent article component, wherein the absorbent article component comprises a first surface and a second surface; and advancing the absorbent article component to a first laser assembly, where the first laser assembly comprises a first laser source positioned adjacent the first surface and a second laser source positioned adjacent the second surface, wherein the first laser source operatively engages the first surface of the absorbent article component imparting a first line of weakness on the first surface of the absorbent article component and the second laser source operatively engages that second surface of the absorbent article component imparting a second line of weakness on the second surface of the absorbent article component, wherein the first line of weakness and the second line of weakness are coincident.

In some embodiments, a method for manufacturing an absorbent article includes the steps of: rotating a first guide roller about a first axis of rotation; rotating a second guide roller about a second axis of rotation, wherein the first guide roller is adjacent the second guide roller; advancing an absorbent article component around a portion of the first guide roller, wherein the absorbent article component comprises a first substrate and a second substrate; disposing the second substrate of the absorbent article component on an outer circumferential surface of the first guide roll; advancing the absorbent article component to a first laser beam, wherein the first laser beam imparts a first line of weakness into the first substrate; advancing the substrate assembly between the first guide roller and the second guide roller; disposing the first substrate of the absorbent article component on an outer circumferential surface of the second guide roll; and advancing the absorbent article component to a second laser beam, wherein the second laser beam imparts a second line of weakness into the second substrate, wherein the second line of weakness is coincident with the first line of weakness.

In some embodiments, a method for manufacturing an absorbent article includes the steps of: advancing an absorbent article component around a portion of a first guide roller, wherein the absorbent article component comprises a first surface and a second surface; advancing the absorbent article component around a portion of a second guide roller, wherein an unsupported portion of the absorbent article component is suspended between the first guide roller and the second guide roller; imparting a first line of weakness into the first surface of the absorbent article component using a first laser beam, wherein the first laser beam acts on the unsupported portion of the absorbent article component between the first guide roller and the second guide roller; imparting a second line of weakness into the second surface of the absorbent article component using a second laser beam, wherein the second laser beam acts on the unsupported portion of the absorbent article component between the first guide roller and the second guide roller; and wherein the first line of weakness is coincident with the second line of weakness.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A;

FIG. 3B is a cross-sectional view of the diaper pant of FIG. 2 taken along line 3B-3B;

FIG. 6D is a photograph of a portion of a cut edge of a substrate;

FIG. 6E is a photograph of a portion of a cut edge of a substrate;

FIG. 7C is a photograph of a portion of a substrate including a line of weakness;

FIG. 7D is a photograph of a portion of a substrate including a line of weakness;

FIG. 12A is a top view of a belt assembly in accordance with one non-limiting embodiment of the present disclosure;

FIG. 12B is a top view of a belt assembly in accordance with one non-limiting embodiment of the present disclosure;

FIG. 13A is a side view of a guide roller in accordance with one non-limiting embodiment of the present disclosure;

FIG. 13B is a partial side view of a belt assembly disposed on a portion of a guide roller in accordance with one non-limiting embodiment of the present disclosure;

FIG. 13C is a schematic side view of a single laser beam imparting a line of weakness into a garment facing layer and a wearer facing layer of a belt assembly in accordance with one non-limiting embodiment of the present disclosure;

FIG. 13D is a schematic side view of a first laser beam imparting a line of weakness into a garment facing layer and a second laser beam imparting a second line of weakness to a wearer facing layer of a belt assembly in accordance with one non-limiting embodiment of the present disclosure;

FIG. 14A is a top view of a belt assembly including a discrete line of weakness in accordance with one non-limiting embodiment of the present disclosure;

FIG. 14B is a top view of a belt assembly including a continuous line of weakness in accordance with one non-limiting embodiment of the present disclosure;

FIG. 14C is an end view of a belt assembly including a first line of weakness and a second line of weakness in accordance with one non-limiting embodiment of the present disclosure;

FIG. 14F is a top view of a belt assembly including a discrete line of weakness and a gap in accordance with one non-limiting embodiment of the present disclosure;

FIG. 15A is a schematic representation of an apparatus that imparts a first line of weakness into a first surface of a first substrate and a second line of weakness into a second surface of a second substrate in accordance with one non-limiting embodiment of the present disclosure;

FIG. 15B is a schematic representation of an apparatus that imparts a first line of weakness into a first surface of a first substrate and a second line of weakness into a second surface of a second substrate in accordance with one non-limiting embodiment of the present disclosure;

FIG. 18A is a top view of a discrete component in a first orientation in accordance with one non-limiting embodiment of the present disclosure;

FIG. 18B is a top view of a discrete component in a second orientation in accordance with one non-limiting embodiment of the present disclosure;

FIG. 18C is a top view of a belt assembly including a discrete component in accordance with one non-limiting embodiment of the present disclosure;

DETAILED DESCRIPTION OF THE INVENTION

Figure 1:
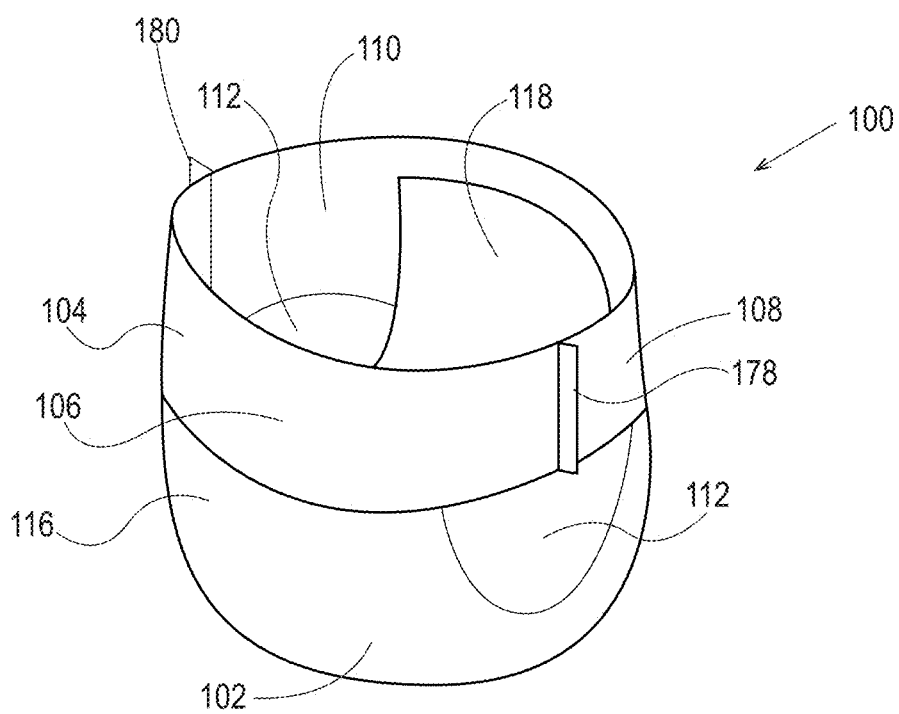
FIG. 1 is a perspective view of a diaper pant.

The following term explanations may be useful in understanding the present disclosure: "Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after an initial use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

The term "extensible" as used herein refers to any material that upon application of a biasing force, can stretch to an elongated length of at least about 110% of its relaxed, original length (i.e. can stretch to 10%), without rupture or breakage, and upon release of the applied force, shows little recovery, less than about 40% of its elongation.

The terms "activating", "activation" or "mechanical activation" refer to the process of making a substrate, or an elastomeric laminate more extensible than it was prior to the process. "Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The term "taped diaper" refers to disposable absorbent articles having an initial front waist region and an initial rear waist region that are not fastened, pre-fastened, or connected to each other as packaged, prior to being applied to the wearer. A taped diaper may be folded about its lateral central axis with the interior of one waist region in surface to surface contact with the interior of the opposing waist region without fastening or joining the waist regions together. Example taped diapers disclosed in various suitable configurations are disclosed in U.S. Pat. Nos. 5,167,897; 5,360,420; 5,599,335; 5,643,588; 5,674,216; 5,702,551; 5,968,025; 6,107,537; 6,118,041; 6,153,209; 6,410,129; 6,426,444; 6,586,652; 6,627,787; 6,617,016; 6,825,393; and 6,861,571.

The present disclosure relates to methods and apparatuses for assembling absorbent articles, and more particularly, methods and apparatuses for using one or more laser sources to create at least two lines of weakness in one or more portions of the components of the absorbent article.

To help provide additional context to the subsequent discussion of the process embodiments, the following provides a general description of absorbent articles in the form of diapers that may be assembled in accordance with the methods and apparatuses disclosed herein. Although the methods and apparatuses herein are discussed below in the context of manufacturing absorbent articles, it is to be appreciated that the assembly methods and apparatuses herein may be configured to manufacture various types of substrates.

Figure 4:
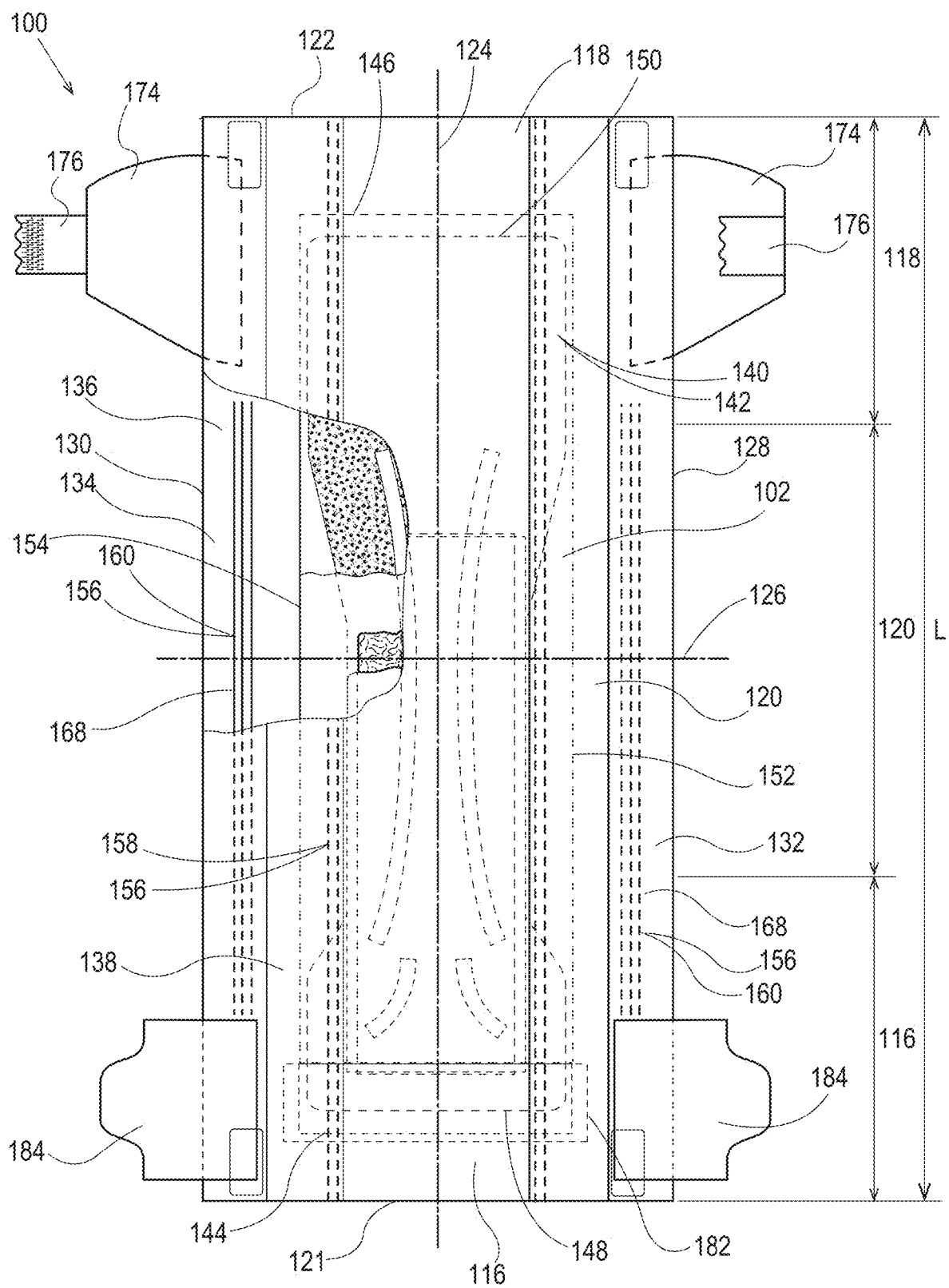
FIG. 4 is a partially cut away plan view of a diaper.

FIGS. 1, 2, and 4 illustrate an example of an absorbent article 100, such as a diaper, that may be assembled with the methods and apparatuses discussed herein. In particular, FIG. 1 shows a perspective view of an absorbent article 100 in a pre-fastened configuration, and FIG. 2 shows a plan view of the absorbent article 100 with the portion of the diaper that faces away from a wearer oriented towards the viewer. The absorbent article 100 shown in FIGS. 1 and 2 includes a chassis 102 and a ring-like elastic belt 104. As discussed below in more detail, a first belt 106 and a second belt 108, which are both elastic, are connected together to form the ring-like elastic belt 104.

With continued reference to FIG. 2, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region 120 may be 1/3 of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the absorbent article 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1, 2, and 4, the absorbent article 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the absorbent article 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. When the absorbent article 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118.

It is also to be appreciated that a portion or the whole of the absorbent article 100 may also be made laterally extensible. The additional extensibility may help allow the absorbent article 100 to conform to the body of a wearer during movement by the wearer. The additional extensibility may also help, for example, allow the diaper 100, including a chassis 102 having a particular size before extension, to extend in the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets, and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916, 661; 6,545,197; and 6,107,539.

The absorbent article 100 may also include an absorbent assembly 140 that is joined to the chassis 102. As shown in FIGS. 2 and 4, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834, 735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core may comprise a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The absorbent article 100 may also include elasticized leg cuffs 156. It is to be appreciated that the leg cuffs 156 may be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. For example, in some embodiments, a gasketing leg cuff 160 may be positioned adjacent to the side edge 130, 128 of the chassis 102 and a barrier leg cuff 158 may be positioned between a gasketing leg cuff 160 and the longitudinal axis 124 of the absorbent article 100. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730 A1; and U.S. Patent Publication No. 2013/0255865 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, the absorbent article may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; discrete strands; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

Referring to FIG. 4, in some embodiments, the absorbent article 100 may include a fastening system. The fastening system can be used to provide lateral tensions about the circumference of the absorbent article to hold the absorbent article on the wearer. The fastening system may comprise a fastener such as tape tabs, hook and loop fastening components, interlocking fasteners such as tabs and slots, buckles, buttons, snaps, and/or hermaphroditic fastening components. A landing zone 182 may be provided on the front waist region 116 for at least a portion of the fastener to be releasably attached to. Exemplary fastening systems may include those described in U.S. Pat. Nos. 3,848,594; 4,662,875; 4,846,815; 4,894,060; 4,946,527; 5,151,092; and 5,221,274.

As illustrated in FIG. 4, the absorbent article 100 may comprise front ears 184 and back ears 174. The front ears 184 and the back ears 174 may be an integral part of the chassis 102. For example, the front ears 184 and the back ears 174 may be formed from the topsheet 138 and/or the backsheet 136. Alternatively, the front ears 184 and the back ears 174 may be attached to the backsheet 136 and/or the topsheet 138. The front ears 184 and the back ears 174 may be extensible to facilitate attachment on the landing zone 182 and to maintain placement around the waist of the wearer. The back ears 174 may comprise a tab member 176. The tab member 176 may be attached to a portion of the back ears 174 to facilitate attachment to the landing zone 182.

As previously mentioned, the methods according to the present disclosure may be utilized to assemble discrete absorbent articles 100 and/or various components of absorbent articles 100, such as for example, chassis 102, elastic belts 106, 108, and/or leg cuffs 156. Although the following methods may be provided in the context of absorbent articles 100, as shown in FIGS. 1, 2, and 4, it is to be appreciated that the methods and apparatuses herein may be used with various process configurations and/or absorbent articles, such as for example, disclosed in U.S. Pat. No. 7,569,039; U.S. Patent Publication Nos. 2005/0107764 A1, 2012/0061016 A1, and 2012/0061015 A1; 2013/0255861 A1; 2013/0255862 A1; 2013/0255863 A1; 2013/0255864 A1; and 2013/0255865 A1.

As previously mentioned, the apparatuses and methods according to the present disclosure may be used to assemble absorbent articles. Various components are used to assemble the absorbent articles. Some of these components may require cutting so that the component is the proper size and/or the proper shape, for example, to be attached to other components. Most of these components, such as the topsheet and the backsheet, are made of nonwovens, as previously disclosed. Absorbent article components may include the individual components of the absorbent article such as a topsheet, backsheet, belt or belt assembly, absorbent assembly, absorbent core, leg cuffs (barrier leg cuffs, gasketing leg cuffs), ears, tab members, and the like. The following disclosure is directed to a belt assembly for purposes of ease of description. However, it is to be appreciated that a laser source may act on any absorbent article component having a substantially planar surface. An absorbent article component may be referred to herein as a discrete component.

A laser source has been one method used to cut these component parts. The laser source may be used to project or emit a laser beam at a scan head which directs the laser beam at the component part, which may be, for example, an advancing substrate. An example of a scan head is the SCANcube III available from SCANLAB America, Inc. of St. Charles, Ill. The laser beam interacts with a portion of the advancing substrate, which may be a nonwoven material, resulting in the cutting of that portion of the advancing substrate. Cutting the advancing substrate results in the substrate being substantially separated into a first portion and a second portion. Each of the first portion and the second portion have a cut edge. The cut edge is the edge formed from the laser source causing the ablation and melting of the nonwoven material. Generally, the more power used by the laser source, the faster the substrate may be cut, and the faster the speed at which the advancing substrate is moving, the more power required to cut the substrate. Thus, due to high manufacturing speeds, cutting substrates using a laser source requires a relatively large amount of power.

However, increasing the power of the laser source may result in degradation of the final cut edge. More specifically, cutting nonwoven components with the use of a laser source may create a rough feeling at the cut edge of the component part. This rough edge is due to the formation of accumulated material. The accumulation of material is due, in part, to the elastic and/or thermal deformation of the nonwoven during the separation of the nonwoven substrate. The individual fibers that are in relatively direct contact with the laser beam are ablated. However, the individual fibers of the nonwoven material along the cut edge or separation edge that do not get ablated undergo melting and/or shrinkage and subsequent cooling. During the subsequent cooling of the separated nonwoven, the fibers along the cut edge snap-back, which also may be described as roll back, resulting in an accumulation of material at the end portion of the nonwoven. Further, one or more fibers may join together to form a cluster of accumulated material. Generally, the greater the power used to separate the nonwoven, the larger the amount of accumulated material and/or clusters at the cut edge. This accumulated material is particularly undesirable for absorbent articles. Absorbent articles are intended to be worn or used in close contact with an individual's skin. Therefore, it is undesirable to have an absorbent article that is perceived to be rough and/or coarse, and which may also result in irritation of the wearer's skin.

It is also to be appreciated that at least a portion of the snap-back, also referred to as roll back, may be due to the processes used to form the nonwoven substrate. The individual fibers used to form the nonwoven substrate may be made by an extrusion process. An extruder forces the individual fibers through a tubular structure resulting in the individual fibers being under some tension. As the fibers are laid down to form the nonwoven substrate, the individual fibers are still under a relative amount of tension. However, when the laser source acts on the individual fibers to separate them, the tension in the individual fibers is release when the individual fiber is separated causing the individual fiber to want to relax. This release of tension and relaxation of the individual fiber may contribute to the accumulation of material at the end of individual fiber that has undergone separation by the laser source. The tension in the individual fiber may only be one or numerous factors that contribute to the accumulation of material at the end of the individual fiber.

Figure 5:
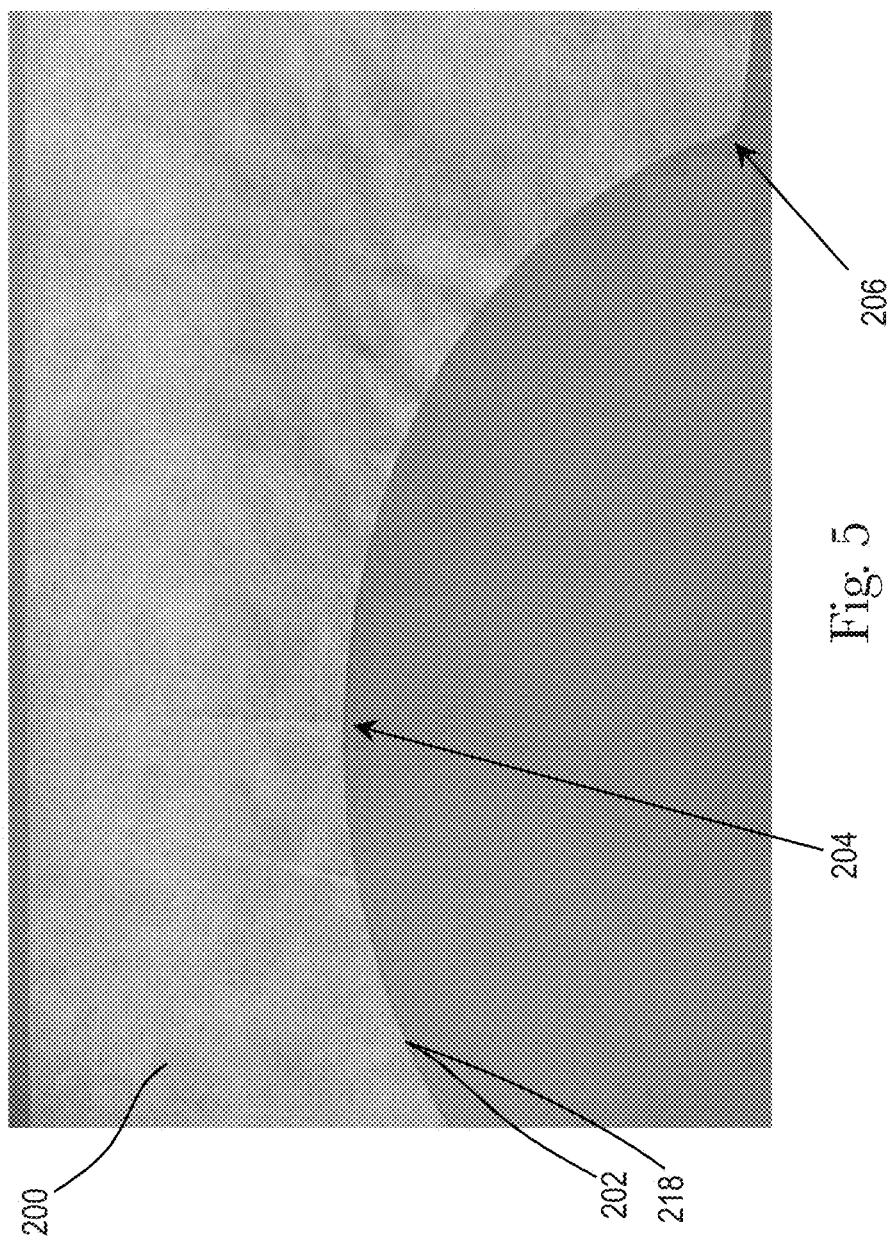
FIG. 5 is a photograph of a portion of a substrate.

FIG. 5 illustrates an example nonwoven substrate 200 including a first layer and a second layer of nonwoven material that has undergone cutting by a laser source or has undergone separating after a line of weakness has been imparted by a laser source. Using a laser source to cut, also referred herein as sever, the substrate 200 in comparison to using the laser source to impart a line of weakness to the substrate and later separate the substrate, results in the edge having relatively different characteristics. As described below, a separation edge may be preferred over a cut edge. It is to be appreciated that a laser source severs or cuts the substrate when the laser alone separates the substrate into a first portion and a second portion along a cut edge. A laser source imparts a line of weakness when the laser source acts on the substrate resulting in the separation of some but not all of the fibers of the nonwoven and a subsequent force may be applied to separate the substrate into a first portion and a second portion.

Figure 6A:
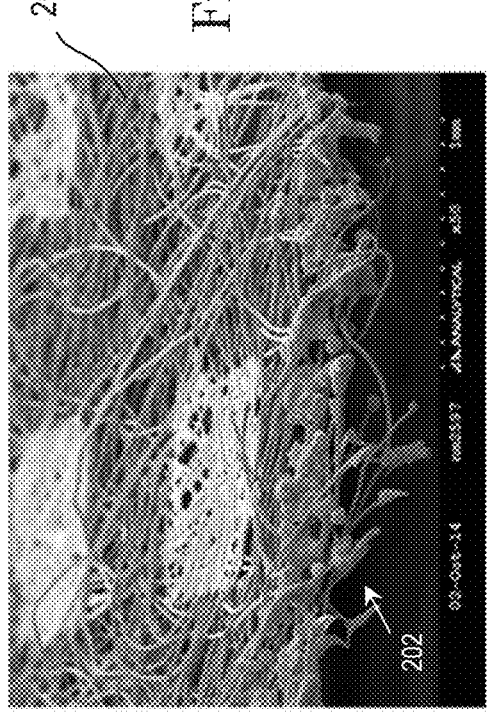
FIG. 6A is a photograph of a portion of a cut edge of a substrate.
Figure 6C:
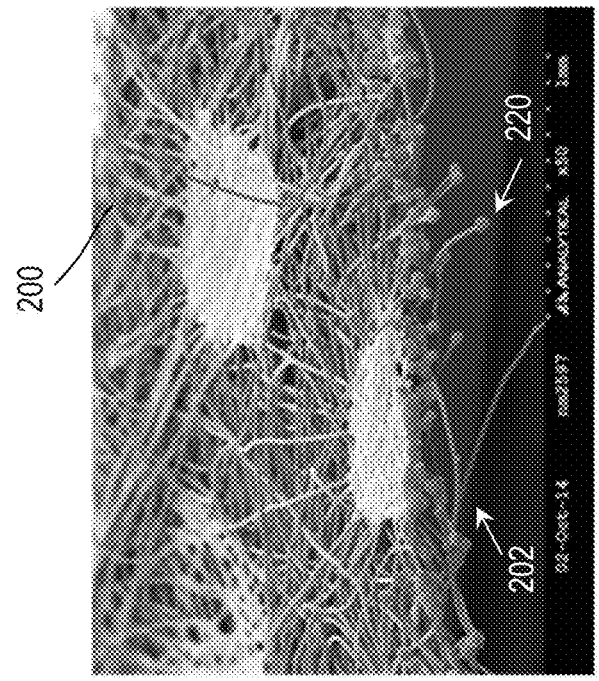
FIG. 6C is a photograph of a portion of a cut edge of a substrate.
Figure 6B:
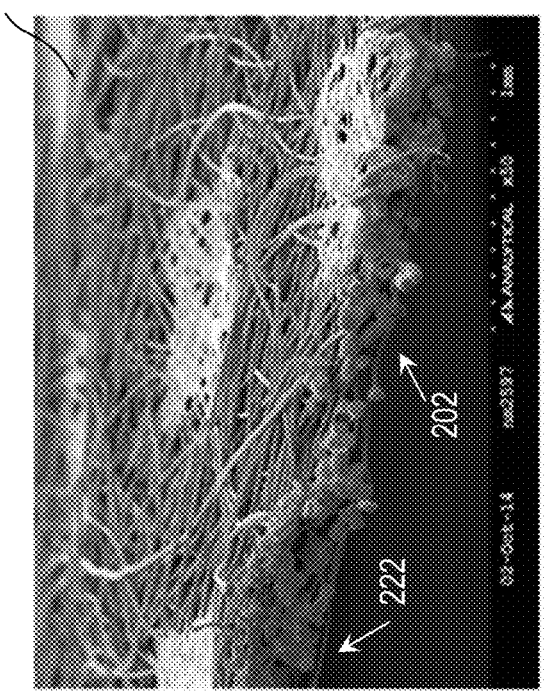
FIG. 6B is a photograph of a portion of a cut edge of a substrate.
Figure 6F:
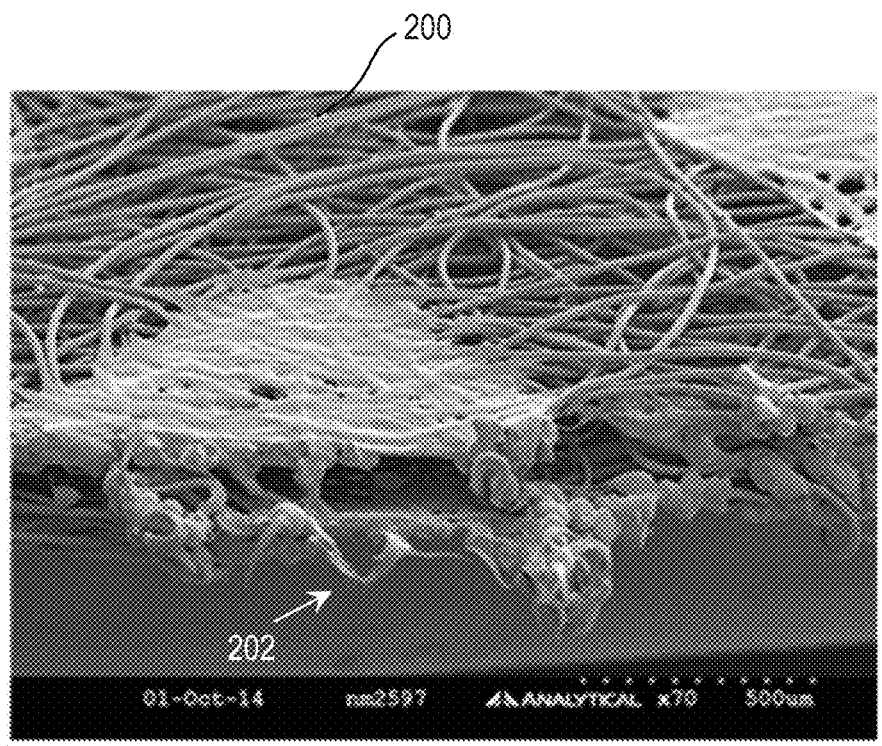
FIG. 6F is a photograph of a portion of a cut edge of a substrate.
Figure 6G:
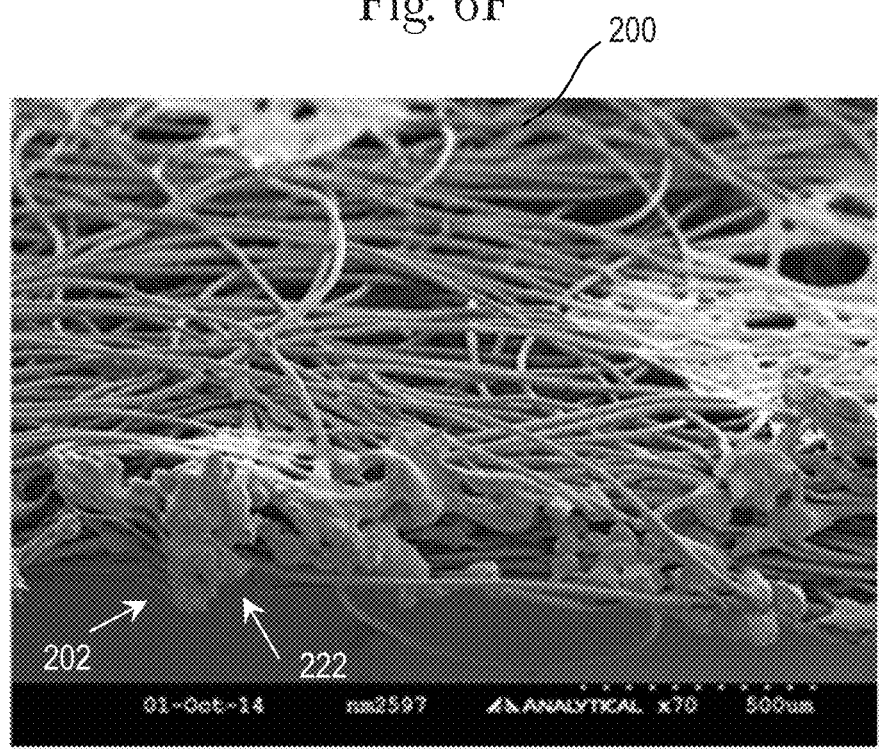
FIG. 6G is a photograph of a portion of a cut edge of a substrate.

The following is a discussion of examples wherein a substrate is cut and the results thereof. The substrate 200 is cut along the cut edge 202, which is illustrated in FIG. 5. The cut edge 202 may include a center portion 204 and an edge portion 206. In this example embodiment, the laser source was operated at 60% of its total power capacity. FIGS. 6A-6H illustrate the characteristics of the cut edge 202 after the substrate 200 was cut with a laser source operating at 60% of its total power capacity. It is to be appreciated that the laser source may be operated at various levels of total power output to cut the substrate 200. FIG. 6A is a perspective edge view of a portion of the substrate 200 at the center portion 204. FIGS. 6B and 6C illustrate the area to the left and right of the edge portion 206. Further, FIGS. 6D and 6E illustrate a portion of a first surface 208 of the substrate 200 and a portion of a second surface 210 of the substrate 200. The arrows in FIGS. 6D and 6E indicate the same area, area A and area B. Further still, FIGS. 6F and 6G illustrate two additional perspective edge views of the cut edge 202. As illustrated in FIGS. 6A-6G, the fibers of the nonwoven material have accumulated material 220 at the end portions and/or along the cut edge. Further, the accumulated material 220 at the end portion of the individual fibers has joined together with the accumulated material 220 of other fibers to form clusters 222 of accumulated material. This accumulated material 220 and clusters 222 of accumulated material make that cut edge feel rough and/or coarse.

In comparison to the aforementioned, it is desirable to have component parts, such as substrates, that are considered to be soft, smooth, and/or non-irritating for use in absorbent articles. Thus, to solve the aforementioned problems, a laser source may be used to impart a line of weakness into the nonwoven substrate 200 rather than to cut through or sever the nonwoven substrate. The line of weakness 212 does not separate the nonwoven substrate 200. After the laser source imparts a line of weakness, a number of nonwoven fibers remain connected. These fibers keep the substrate from separating, and an additional force is required to separate the nonwoven substrate into a first portion and a second portion.

In this example embodiment, the laser source was operated at 25% of its total power capacity. FIGS. 7A-7D, 8, 9A-9B, and 10A-10B illustrate the characteristics of the separation edge 204 after a laser source operating at 25% of its total power capacity imparts a line of weakness into the substrate 200. It is to be appreciated that the laser source may be operated at various levels of total power output to impart a line of weakness to the substrate.

Figure 7A:
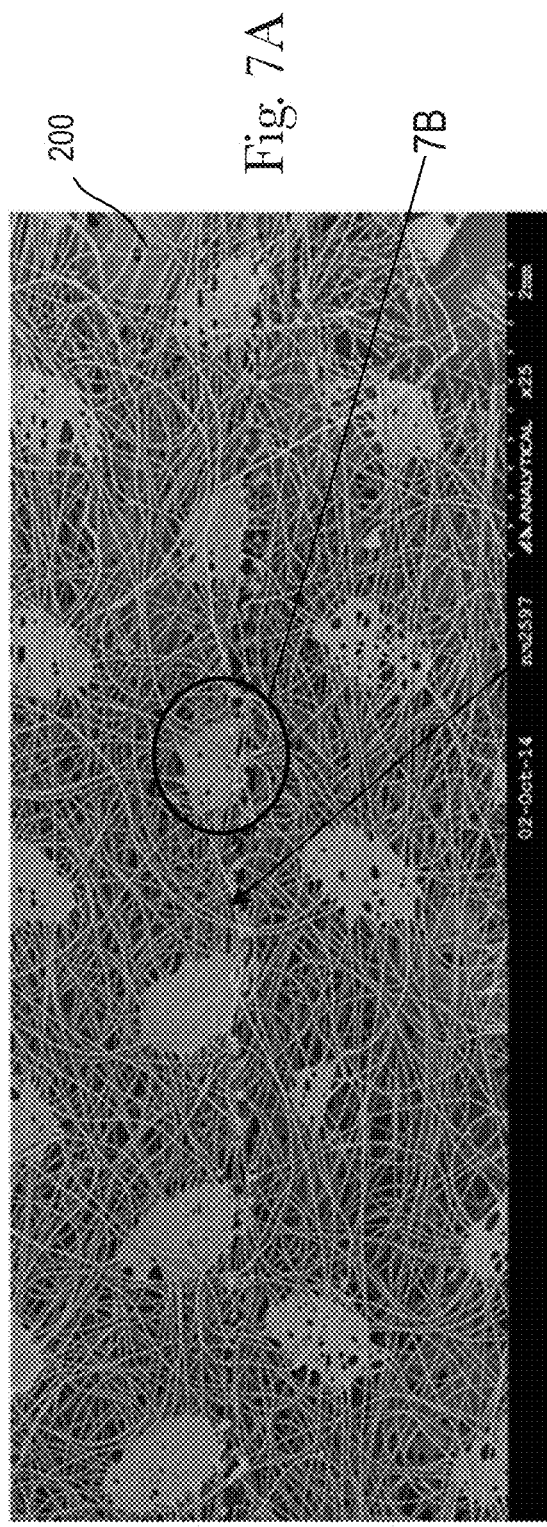
FIG. 7A is a photograph of a portion of a substrate including a line of weakness.
Figure 7B:
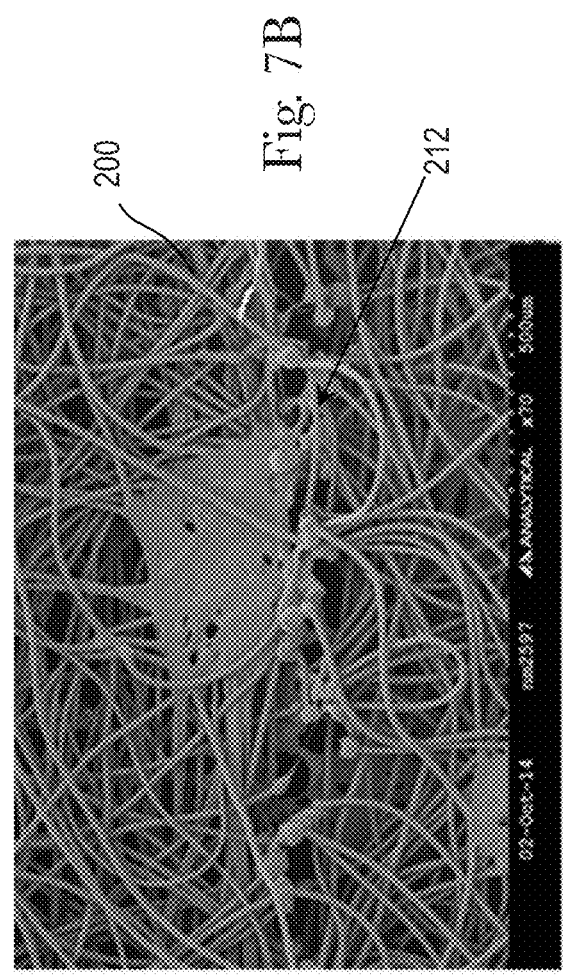
FIG. 7B is a photograph of a portion of a substrate including a line of weakness.
Figure 8:
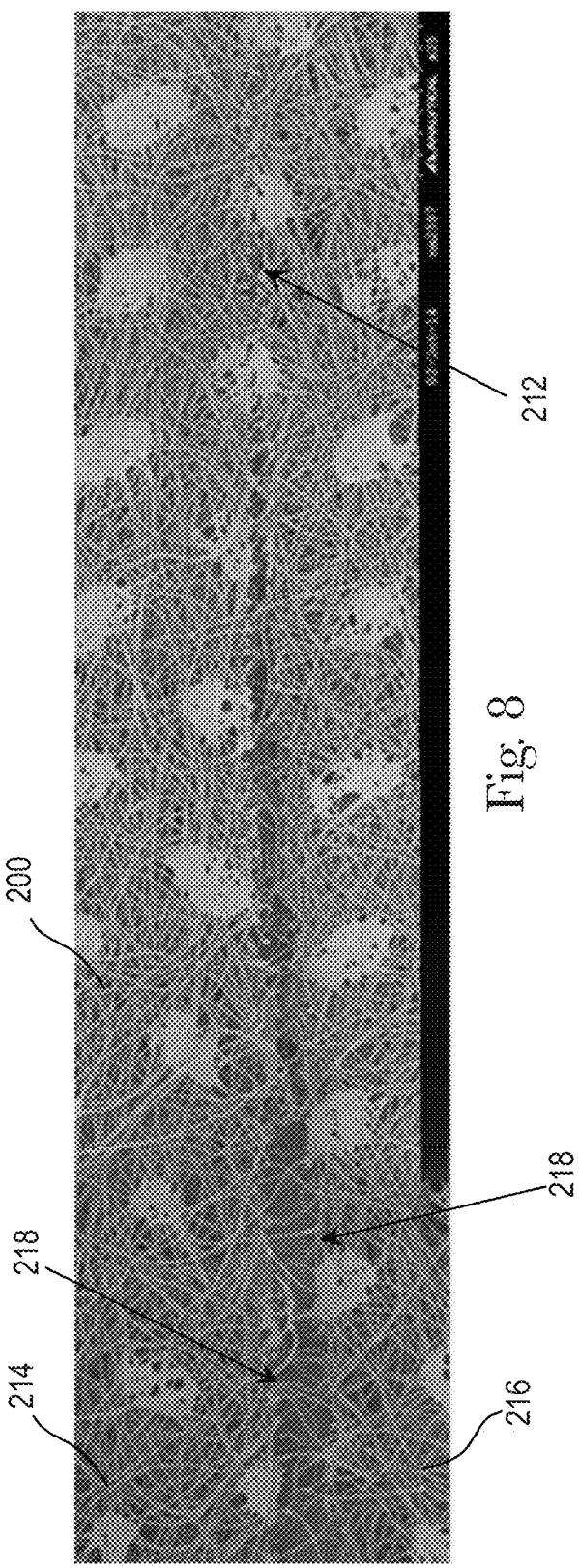
FIG. 8 is a photograph of a portion of a substrate including line of weakness.
Figure 9B:
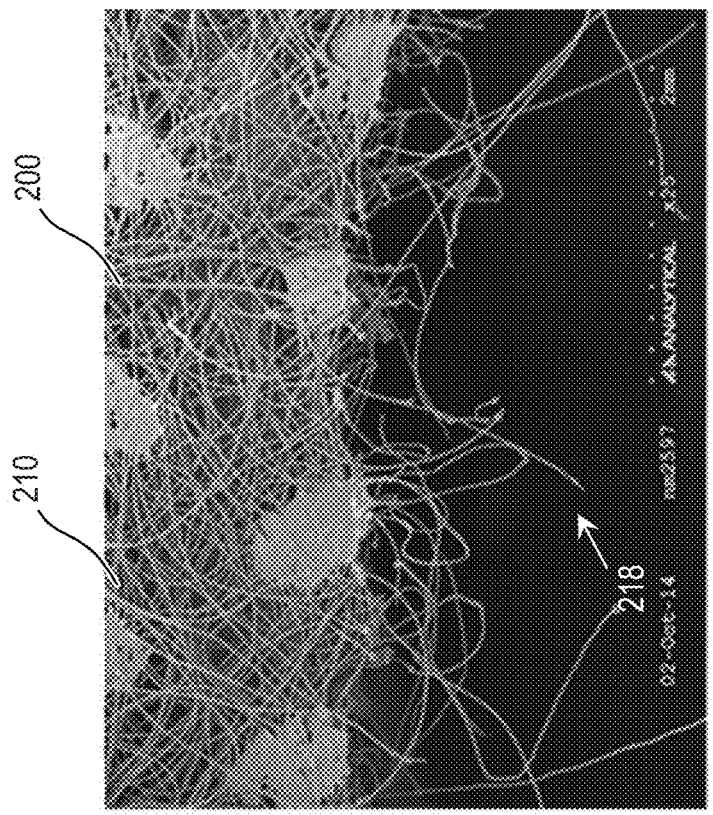
FIG. 9B is a photograph of a portion of a substrate including a separation edge.
Figure 9A:
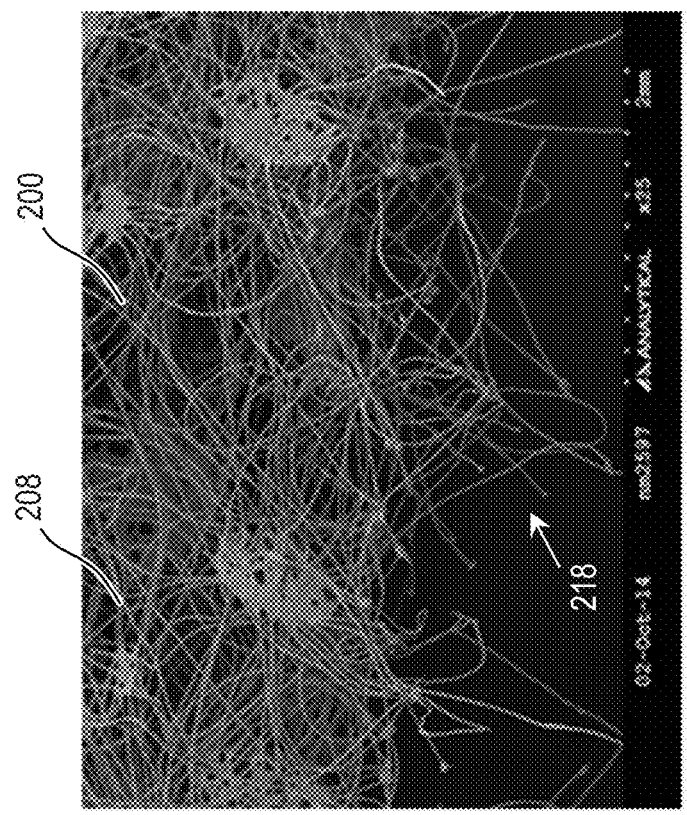
FIG. 9A is a photograph of a portion of a substrate including a separation edge.
Figure 10A:
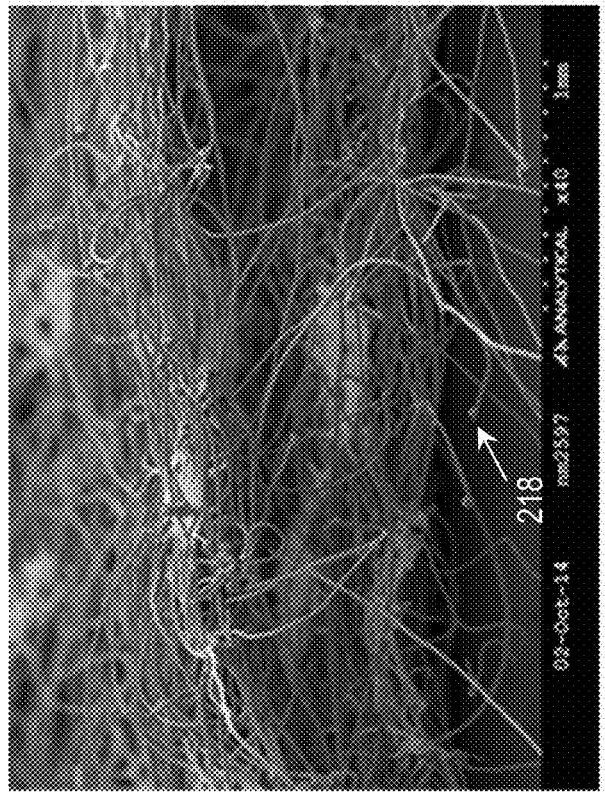
FIG. 10A is a photograph of a portion of a substrate including a separation edge.
Figure 10B:
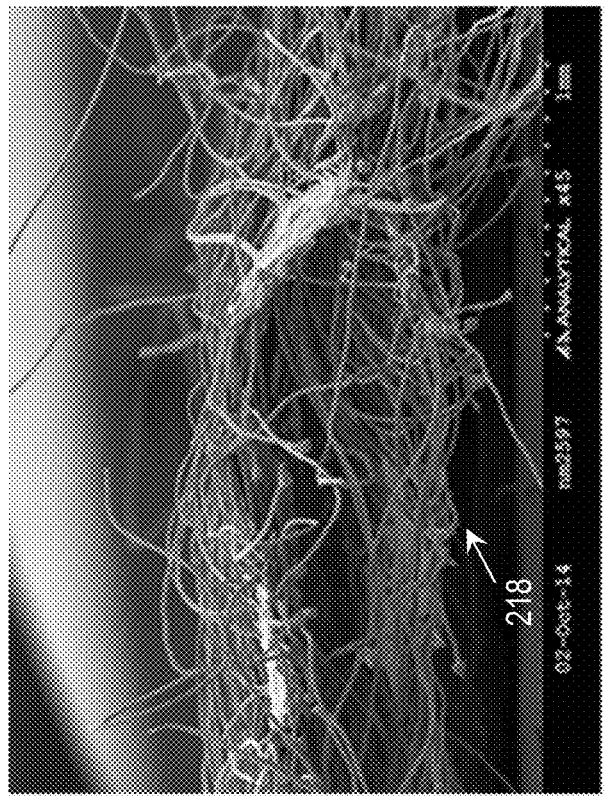
FIG. 10B is a photograph of a portion of a substrate including a separation edge.

FIGS. 7A and 7B illustrate a line of weakness 212 imparted by a laser source onto the substrate 200. FIG. 7B is a magnified view of the area indicated in FIG. 7A. Similarly, FIGS. 7C and 7D show another portion of the substrate that has a line of weakness 212. FIG. 7D is a detailed view of the portion of the line of weakness 212 as indicated in FIG. 7C. After the laser source imparts a line of weakness 212 into the substrate 200, the substrate 200 may be separated along the line of weakness 212 such that the substrate is separated into a first portion 214 and a second portion 216. FIG. 8 illustrates the separation of the substrate 200 along the line of weakness 212 creating a separation edge 218 along both the first portion 214 and the second portion 216. FIGS. 9A and 9B illustrate a first surface 208 and a second surface 210 of a portion of the substrate 200 after separation along the separation edge 218. FIGS. 10A and 10B illustrate a perspective edge view of a portion of the separation edge 218.

As evidenced by the Figures, the separation edge 218 includes less material accumulation than the cut edge 202, as shown in FIGS. 6A-6G. The reduction in material accumulation leads to the separation edge 218 being perceived as softer and/or smoother. Further, the separated edge 218, as evidence by the Figures, has a greater number of fibers that have been loosened during separation at the separation edge 218. These loosened fibers also may contribute to the softer and/or smoother feel of the substrate 200 at the separation edge 218.

The present disclosure relates to a method and apparatus to overcome the aforementioned deficiencies of cutting while utilizing a laser source, and to manufacture a substrate and/or other component parts that are perceived to be softer and/or smoother as compared to similar substrate and/or other component parts that have undergone cutting by a laser source.

Figure 11B:
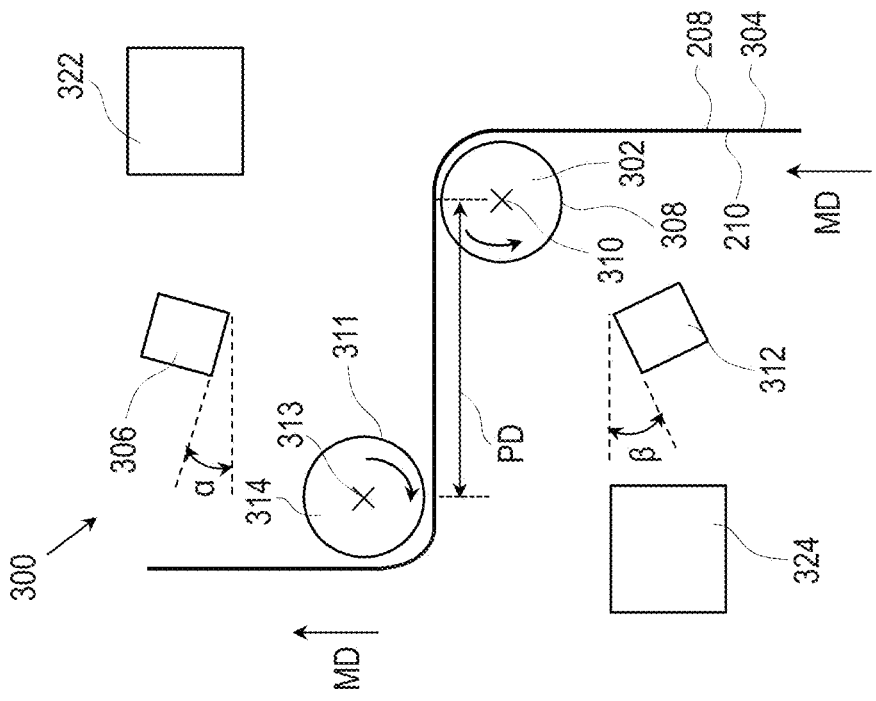
FIG. 11B is a schematic representation of an apparatus that imparts a first line of weakness into a first surface of a first substrate and a second line of weakness into a second surface of a second substrate in accordance with one non-limiting embodiment of the present disclosure.
Figure 11A:
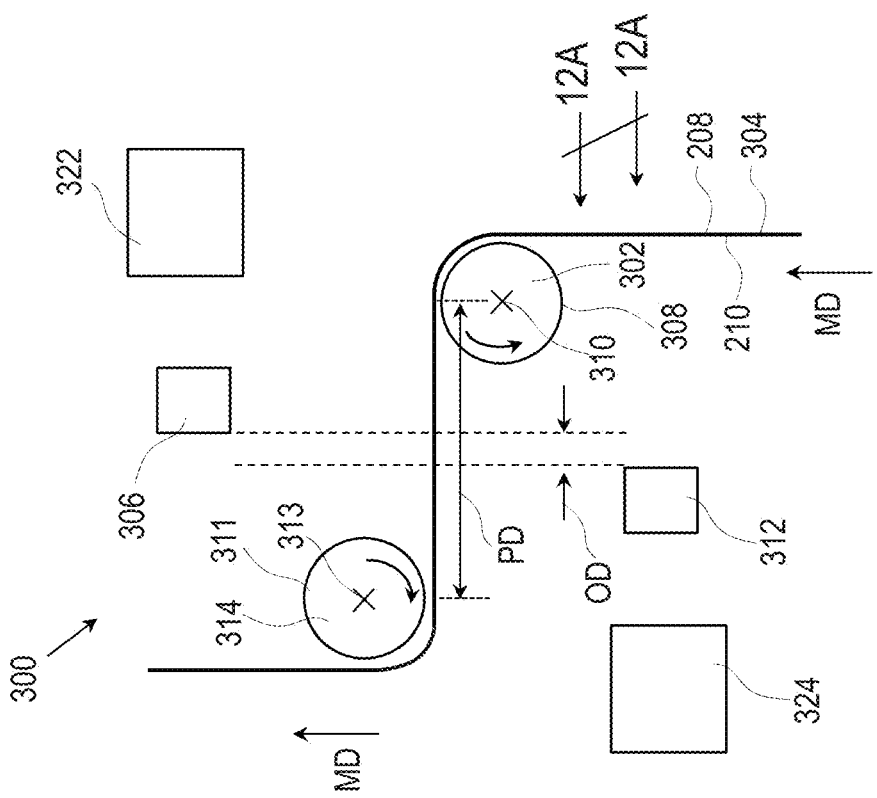
FIG. 11A is a schematic representation of an apparatus that imparts a first line of weakness into a first surface of a first substrate and a second line of weakness into a second surface of a second substrate in accordance with one non-limiting embodiment of the present disclosure.

FIG. 11A illustrates an exemplary schematic representation of an apparatus 300 that may be used in the manufacture of an absorbent article 100, as previously described. The apparatus 300 may include a first guide roller 302. The first guide roller 302 may rotate about a first axis of rotation 310. The first guide roller 302 may be driven by a motor or may rotate freely about the first axis of rotation 310. Further, the first guide roller 302 may be configured to receive a belt assembly 304. It is to be appreciated that a belt assembly is used to describe the process and apparatus herein, but any single layer substrate, laminate, multiple layer substrate, and/or other absorbent article component, as previously discussed, may be used in the process and apparatus discussed herein. The belt assembly 304 may include a first surface 208 and a second surface 210, opposite the first surface 208. These surfaces may be referred to herein as a garment facing layer 162 and a wearer facing layer 164. The belt assembly 304 may advance in a machine direction MD toward the first guide roller 302. The belt assembly 304 may be disposed on a portion of an outer circumferential surface 308 of the first guide roll 302. More specifically, the second surface 210 of the belt assembly 304 may be disposed on the outer circumferential surface 308 of the first guide roll 302.

The first guide roll 302 may rotate about the first axis of rotation 310 resulting in the belt assembly 304 advancing toward at least one of a first laser source 322 and a second laser source 324. The first laser source 322 and the second laser source 324 may be used to impart a discrete line of weakness into the belt assembly 304 and/or to impart a continuous line of weakness into the belt assembly 304. More specifically, the first laser source 322 may transmit a first laser beam to a first scan head 306. The first scan head 306 may direct the first laser beam such that the first laser beam engages the substrate. Similarly, the second laser source 324 may transmit a second laser beam to a second scan head 312. The second scan head 312 may direct the second laser beam such that the second laser beam engages the substrate. It is to be appreciated that a single laser source may be used to emit both the first laser beam and the second laser beam.

The first scan head 306 may be offset from the second scan head 312 may an offset distance OD. The offset distance OD may be any distance such that the first laser beam does not interfere with the second scan head 312 and the second laser beam does not interfere with the first scan head 306. The offset of the first scan head 306 and the second scan head 312 may prevent the opposing laser beam from potentially being directed back to the laser source through the scan head and causing damage to the laser source and/or the scan head. However, it is to be appreciated that the first scan head 306 and the second scan head 312 need not be offset from one another. In some embodiments, the first scan head 306 may be positioned parallel to the second scan head 312.

The first laser source 322 may supply a first laser beam to the first scan head 306. The first scan head 306 directs the first laser beam such that the first laser beam imparts a first line of weakness in the first surface 208 of the belt assembly 304. The second laser source 324 may supply a second laser beam to the second scan head 312. The second scan head 312 directs the second laser beam such that the second laser beam imparts a second line of weakness into the second surface 210 of the belt assembly 304. The first line of weakness may be coincident with the second line of weakness. The first line of weakness is coincident with the second line of weakness when the first line of weakness and the second line of weakness are separated by a distance less than about 2 mm and/or less than about 1.5 mm and/or less than about 1 mm and/or less than about 0.5 mm, including all 0.1 increments.

The belt assembly 304 may be advanced to a second guide roller 314. The belt assembly 304 that is positioned between the first guide roller 302 and the second guide roller 314 is referred to herein as the unsupported portion. The unsupported portion is the area of the belt assembly 304 on which the first laser beam and the second laser beam may affect the belt assembly 304. The distance between the first guide roll 302 and the second guide roll 314 is referred to herein as the process distance PD. The process distance PD may be such that the unsupported portion of the belt assembly remains substantially taut as the first line of weakness and the second line of weakness are imparted by the laser beams. The process distance PD may be any distance that allows the first line of weakness and the second line of weakness to be imparted into the belt assembly such that the first line or weakness and the second line of weakness are coincident and are positioned in the desired location. In some embodiments, for example, the process distance PD may be less than about 3 times the substrate width SW and/or less than about 2 times the substrate width SW and/or less than about the substrate width SW and/or less than about 0.5 times the substrate width SW and/or less than about 0.25 times the substrate width SW. The substrate width SW, as illustrated in FIGS. 12A and 12B, is the width extending parallel to the cross direction CD from each outside edge of the belt assembly 304.

The second guide roller 314 may be used to advance the belt assembly 304 to one or more subsequent processes and/or to maintain the tension and/or position of the belt assembly. The second guide roller 314 may rotate about a second axis of rotation 313. The second guide roller 314 may be driven by a motor or may rotate freely about the second axis of rotation 313. The belt assembly 304 may be disposed about an outer circumferential surface 311 of the second guide roller 314. The first surface 208 of the belt substrate 304 may be in facing relationship with the outer circumferential surface 311 of the second guide roller 314. This process and apparatus will be described in more detail herein. The belt assembly 304 having at least one of a continuous line of weakness and a discrete line of weakness may advance to additional processes such as separating the discrete trim portion and/or the continuous trim portion from the belt assembly 304 and/or adding additional components to the belt assembly 304.

It is to be appreciated that the belt assembly may be positioned such that the first surface of the belt assembly engages the outer circumferential surface of the first guide roller and the second surface of the belt assembly engages the outer circumferential surface of the second guide roller.

As illustrated in FIG. 11B, the first scan head 306 and the second scan head 312 may each be at an angle. The first scan head 306 may be at a first angle α with respect to the machine direction MD. The first angle may be from 0 degrees to about 20 degrees and/or from about 2 degrees to about 15 degrees and/or from about 5 degrees to about 10 degrees, including all 0.1 increment therebetween. The second scan head 312 may be at a second angle 13 with respect to the machine direction MD. The first angle may be from about 0 degrees to about 20 degrees and/or from about 2 degrees to about 15 degrees and/or from about 5 degrees to about 10 degrees, including all 0.1 increments therebetween. The first scan head 306 and the second scan head 312 may each be positioned at an angle so that the first laser beam does not interfere with the second scan head 306 and/or the second laser source 324 and the second laser beam does not interfere with the first scan head 306 and/or the first laser source 322. It is to be appreciated that it is not necessary that either the first scan head or the second scan head be at an angle. Each of the first scan head 306 and the second scan head 312 may be positioned substantially perpendicular to the machine direction MD and/or a surface of the belt assembly, as illustrated in FIG. 11A.

Referring to FIG. 12A, the belt assembly 304 may include a first belt 106 and a second belt 108. The first belt 106 and the second belt 108 may be spaced such that an absorbent core or other discrete component may be disposed across a portion of the first belt 106 and the second belt 108. The first belt 106 and the second belt 108 may each include an outer layer 162, an inner layer 164 disposed in facing relationship with the outer layer 162, and elastic strands 168 disposed between the outer layer 162 and the inner layer 164. The elastic strands 168 may be stretched in the machine direction MD and bonded with the first substrate layer 162 and/or the second substrate layer 164. More particularly, the elastic strands 168 may be continuously bonded with the first substrate layer 164 and/or the second substrate layer 162 with adhesive along the machine direction MD and/or the elastic strands 168 may be intermittently bonded with the first substrate layer 162 and/or the second substrate layer 164 with adhesive along the machine direction MD. Thus, the elastic strands 168 may include non-bonded regions along the machine direction MD. The elastic strands are not bonded to either of the first substrate 162 or the second substrate 164 in the non-bonded region. It is to be appreciated that adhesive may also be applied to the first and second substrates 162, 164 between the elastic strands 168.

In some embodiments, as illustrated in FIG. 12B, the belt assembly 304 may include a unitary, body substrate 316. The body substrate 316 may include an outer layer 162, an inner layer 164 disposed in facing relationship with the outer layer 162, and one or more elastics 168 disposed between the outer layer 162 and the inner layer 164. The elastic strands 168 may be stretched in the machine direction MD and bonded with the first substrate layer 162 and/or the second substrate layer 164. As previously discussed, the elastic strands may be continuously bonded or intermittently bonded.

It is to be appreciated that the outer layer 162 and the inner layer 164 may each be made up of one or more layers that have different properties, such as the type of fiber, additives, and density. The properties of the outer layer 162 and the properties of the inner layer 164 may make it advantageous to have one layer or the other layer in closer proximity to, or facing relationship with, to the laser source.

It is also to be appreciated that the characteristics of the separation edge may make it advantageous to have either the outer layer 162 or the inner layer 164 in facing relationship with the laser source. More specifically, as illustrated in FIGS. 7A-7D, 9A-9B, and 10A-10B, the separation edge may still include a portion of individual fibers having accumulated material at the end. The portion of fibers having accumulated material may be greater on one layer as opposed to the adjacent layer. Thus, the layer having a greater portion of accumulated material may be positioned on the absorbent article such that it reduces or eliminates contact with the wearer's skin, and the layer having a lesser portion of accumulated material by be positioned on the absorbent article such that it may contact the wearer's skin. Minimizing the portion of the inner layer 164 or outer layer 162 having the greater amount of accumulated material at the ends of the individual fibers may aid in the perceived softness of the layers. The process and apparatus described herein may act on either the inner layer 164 or the outer layer 162 of a substrate.

In some embodiments, the elastic strands 168 may be positioned in a certain location on the outer circumferential surface 308, 311 of each of the first guide roller 302 and the second guide roller 314. Thus, one or both of the outer circumferential surfaces of the first guide roller and the second guide roller may include one or more grooves 320 into which the elastic stands 168 may be disposed and each of the first guide roller and the second guide roller may be operatively connected to a vacuum source to aid in maintaining the position of the belt assembly, as illustrated in FIGS. 13A and 13 B. At least one of the first outer circumferential surface 308 and the second outer circumferential surface 311 may include one or more apertures 318 configured to transfer air toward the longitudinal axis of rotation 310, 313. A vacuum source, not shown, may be in fluid communication with each of the one or more apertures. The vacuum source allows fluid to be circulated through the one or more apertures toward the first axis of rotation 310, 313. The movement of fluid may result in the belt assembly 304 being forced toward the outer circumferential surface. Thus, the one or more apertures 318 may aid in transferring the belt assembly 304 onto the outer circumferential surface 308, 311 and keeping the belt assembly 304 in position during advancement of the belt assembly and processing of the belt assembly.

Further, at least one of the first outer circumferential surface 308 and the second outer circumferential surface 311 may include one or more grooves 320. The one or more grooves may surround the outer circumferential surface 308, 311 such that the groove extends about the axis of rotation 310, 313. All or some of the grooves may extend only partially around the axis of rotation 310, 313. Stated another way, the grooves 320 may be placed such that there are ungrooved portions between and adjacent to groove portions. Further, the grooves may be spaced in the cross direction such that there is a uniform distance between each groove 320. It is also to be appreciated that the grooves 320 may be spaced in the cross direction such that there is a non-uniform distance between each groove 320, as illustrated in FIG. 13A. The grooves may be spaced in the cross direction CD such that each groove corresponds to the desired spacing of the elastic strands 168. The outer circumferential surface 308, 311 may include any number of grooves 320 that allow the belt assembly 304 to remain in a desired position during advancement of the belt assembly 304 and/or to locate one or more of the elastic strands 168 in the belt assembly 304 for processing. For example, to locate the elastic strands 168, the outer circumferential surface 308 may include a number of grooves 320 into which the elastic strands 168 are positioned as the belt assembly 304 is transferred onto the process member 302. FIG. 13B illustrates a portion of the outer circumferential surface 308, 311 including one or more grooves 320 into which the elastic strands 168 are positioned. It is to be appreciated that the grooves may be any shape such as semi-circular, triangular, hexagonal, trapezoidal, or any other shape that inhibits movement of the elastic strands and/or maintains the location of the elastic strands 168 about the outer circumferential surface 308, 311.

As previously discussed, the accumulation of material and/or clusters along the separation edge may be minimized by imparting a line of weakness to a substrate rather than cutting the substrate. The belt assembly 304 may include a garment facing layer 162 and a wearer facing layer 164, in facing relationship with the garment facing layer 162, as illustrated in FIGS. 13C and 13D. Referring to FIG. 13C, if a single laser beam 372 engages the belt assembly 304, the laser beam 372 must ablate and/or melt the garment facing layer 162 and a portion of the wearer facing layer 162. More specifically, in order to separate both the garment facing layer 162 and the wearer facing layer 164, the laser beam 372 must ablate all the material in the substrate positioned proximal to the laser source so that the laser beam can reach the second, lower layer substrate and ablate and/or melt a portion of the second, lower layer substrate. The laser source must operate at a power such that the thickness t of the first substrate is ablated and/or melted and a portion of the second substrate is ablated and/or melted. Due to the need for more power, a relatively greater amount of material accumulation and clusters form along the separation edge of the substrates.

FIG. 13D minimizes the accumulation of material and/or clusters as compared to that described with respect to FIG. 13C by using two laser sources. A first laser beam 372 may engage the garment facing layer 162 of the belt assembly 304. The first laser beam 372 need only ablate and/or melt a portion of the thickness of the garment facing layer 162 to form a first line of weakness. Similarly, a second laser beam 374 may engage the wearer facing layer 164 of the belt assembly 304. The second laser beam 374 need only ablate and/or melt a portion of the thickness of the wearer facing layer 164 to form a second line of weakness. The first line of weakness may be coincident with the second line of weakness such that when the trim is separated along the separation edge, the belt assembly separates along each of the lines of weakness and not along other portions of the belt assembly. Further, because each of the first laser beam and the second laser beam need only ablate and/or melt a portion of thickness of each substrate, the power at which each laser source(s) operates may be reduced relative to the power required to ablate and/or melt two substrates from a single direction. The total power required to impart the first and second lines of weakness using two laser beams each acting on the substrates independently is less than the power required for a single laser source to impart a single line of weakness from a single direction into a first and second substrate. Further still, because the laser source(s) described with respect to FIG. 13D operates at a relatively lower power, the separation edge may include relatively fewer amounts of accumulated material and/or clusters. Minimizing the amount of accumulated material and/or clusters produces a separation edge that is perceived as softer feeling and more appealing to consumers.

It is also to be appreciated that in addition to requiring lower power output to impart the first and second lines of weakness, the first and second lines of weakness are coincident. As previously discussed coincident lines of weakness may be separated by a distance less than about 2 mm and/or less than about 1.5 mm and/or less than about 1 mm and/or less than about 0.5 mm, including all 0.1 increments. The separation in the coincident lines of weakness may also contribute to the perceived feeling of softness and to the appeal of consumers.

As previously discussed, a laser source may be used to impart a line of weakness into the belt assembly 304. A line of weakness refers to any line, region, or area of weakened material, and may include linear and non-linear lines or patterns, such as curvilinear lines and patters of weakness, or other shapes, such as circles, rectangles, or triangles. A laser source forms a line of weakness by causing some of the fibers of the nonwoven material to separate, but not causing all the fibers of the nonwoven material to separate. Thus, after the laser source acts on the belt or substrate, the substrate remains attached at certain locations but has become detached at other locations. The power of the laser source and the properties of the substrate determine how much of the substrate remains attached after the laser source imparts the line of weakness. A line of weakness may be a discrete line of weakness or a continuous line of weakness. A discrete line of weakness may be a line that includes a first end point and a second end point within the length of two product pitches. A continuous line of weakness may be a line that continues over the length of two or more product pitches. A product pitch PP is the length of the discrete substrate after the continuous substrate is cut into discrete portions. An example of a product pitch PP is illustrated in FIG. 18C. The product pitch is measured between a first cut line and an adjacent, second cut line parallel to the edge 232 of the substrate, which may be a belt assembly 304, as illustrated in FIG. 18C. It is to be appreciated that more than one laser source and associated scan head(s) may be used to impart a continuous line of weakness.

As illustrated in FIGS. 14A and 14C, one or more laser sources may be used to impart a discrete line of weakness into the belt assembly. More specifically, for example, a first laser source 322 may be positioned adjacent the first belt 106 and a third laser source 326 may be positioned adjacent the second belt 108. The first laser source 322 may be used to impart discrete lines of weakness 224 into the first belt 106. The third laser source 326 may be used to impart discrete lines of weakness 224 into the second belt 108. The first laser source 322 emits a first laser beam to engage the wearer facing layer 162 of the first belt 106 forming discrete lines of weakness 224 in the wearer facing layer 162. The third laser source emits a third laser beam to engage the wearer facing layer 162 of the second belt 108 forming discrete lines of weakness in the wearer facing layer 162. It is to be appreciated that a second laser source 324 and a fourth laser source 328 may each be used to impart discrete lines of weakness on the garment facing surface 162 of each of the first belt 106 and the second belt 108 as described above. Each of the first laser source 322, the second laser source 324, the third laser source 326 and the fourth laser source 328 may be powered on and off to create each discrete line of weakness. As the belt assembly 304 advances in the machine direction, each laser source may power on to impart a discrete line of weakness and subsequently power off until the belt assembly 304 advances to a position where a second discrete line of weakness needs to be imparted onto the belt assembly. Each discrete line of weakness 224 may have characteristics such as the line of weakness 212 described with respect to FIGS. 7A-7D, 9A-9B, and 10A-10B.

It is also to be appreciated that a discrete line of weakness may also be imparted to the substrate by a laser that remains powered on. For example, the laser source may remain powered on but may be diverted to a position adjacent the edge of the substrate. More specifically, the laser source may remain powered on while the substrate advances in the machine direction. As the substrate advances, the laser beam of the laser source may be diverted such that it imparts a discrete line of weakness and, subsequently, may be diverted again such that the laser beam is adjacent the edge of the substrate or, state another way, does not act on the substrate.

Further, the power output of the laser source may be adjusted while the laser source is powered on or while the laser source is powered off. For example, a first discrete line of weakness may be imparted to the belt assembly at a first power output and a second discrete line of weakness may be imparted to the belt assembly at a second power output, wherein the first power output is greater than or less than the second power output. The power output of the laser source may also be adjusted while imparting a single, discrete line of weakness. More specifically, the laser source may impart a portion of the discrete line of weakness at a first power output and impart another portion of the discrete line of weakness at a second power output, which is greater than or less than the first power output. For example, a belt assembly may include a first portion including a single substrate layer and a second portion including more than one substrate layer, such as two or three substrate layers. A discrete or continuous line of weakness may be required to be imparted over both the first portion and the second portion of the belt assembly. Thus, the laser source may operate at a first power output as it imparts the line of weakness over the first portion including only a single substrate layer and the laser source may operate at a second power output, which is different than the first power output, as it imparts the line of weakness over the second portion including several substrate layers. The laser source may be adjusted from the first output power to the second output power while it is powered on and imparting the line of weakness into the belt assembly. The power output of the laser source may increase as the number of layers of substrate into which the line of weakness needs to be imparted increases. It is to be appreciated that there may be one or more laser sources depending on the type of cut and/or line of weakness that needs to be imparted to the belt assembly 304 and the material properties of the belt assembly.

It is to be appreciated that the speed at which the laser beam moves about the substrate may be varied in addition to the power output or independent of the power output. For example, the speed of the laser beam may be altered such that the laser beam imparts imperceptible changes to the substrate. More specifically, the laser beam may be moved so quickly with respect to the moving or stationary substrate that the laser beam is unable to dwell on the surface of the substrate long enough to impart any perceptible change to the substrate. The laser beam may then be slowed relative to the moving or stationary substrate when the laser beam reaches a desired position on the substrate. Slowing the rate of the laser beam relatively to the substrate may allow the laser beam to impart, for example, a line of weakness.

It is also to be appreciated that the focal area of the laser beam may be varied. The focal area is determined by the spot size diameter and focal length. For example, the scan head may be configured such that the laser beams focal area on the substrate may be widened and narrowed. For example, when the focal area of the laser beam is widened such that the laser beam covers a greater area of the substrate, the laser beam is unlikely to affect the substrate. As the focal area of the laser beam is narrowed, becoming concentrated over a relatively smaller area of the substrate, the more likely that the laser beam may affect the substrate. Thus, the focal area of the laser beam may be widened over portions of the substrate that are desired to be unaffected or minimally affected by the laser beam, and the focal area of the laser beam may be narrowed over portions of the substrate that are desired to be affected by the laser beam.

The speed of the laser beam, the power output of the laser source, and the focal area of the laser beam are all variables that may be altered to impart a line of weakness into a surface of a substrate. Altering any one of these variables may change the characteristics of the line of weakness.

The line of weakness may be a continuous line of weakness, as illustrated in FIG. 14B. A first laser source 322 may be positioned adjacent the first belt 106 and a third laser source 326 may be positioned adjacent the second belt 108. The first laser source 322 may be used to impart a continuous line of weakness 226 into the first belt 106. The third laser source 326 may be used to impart a continuous line of weakness 226 into the second belt 108. The continuous lines of weakness 226 may have characteristics such as the line of weakness 212 described with respect to FIGS. 7A-7D, 9A-9B, and 10A-10B. It is to be appreciated that the power output of the laser source 322, 326 may be adjusted while the laser source is imparting the continuous line of weakness onto the belt assembly, as previously described. In addition, in order to ensure separation of the trim portion of the line of weakness, the power output of the laser source may need to be increased around curved or non-linear portions of the continuous line of weakness. This may cause more of the fibers in these regions to separate making it easier to separate and remove the trim from the belt assembly along the continuous line of weakness. Further, as described above with respect to FIG. 14A, the configuration in FIG. 14B may also include a second laser source 324 and a fourth laser source 328 positioned adjacent the opposite surface of the belt assembly as the first and third laser source and configured to impart a second continuous line of weakness that may be coincident with the first line of weakness.

Figure 14D:
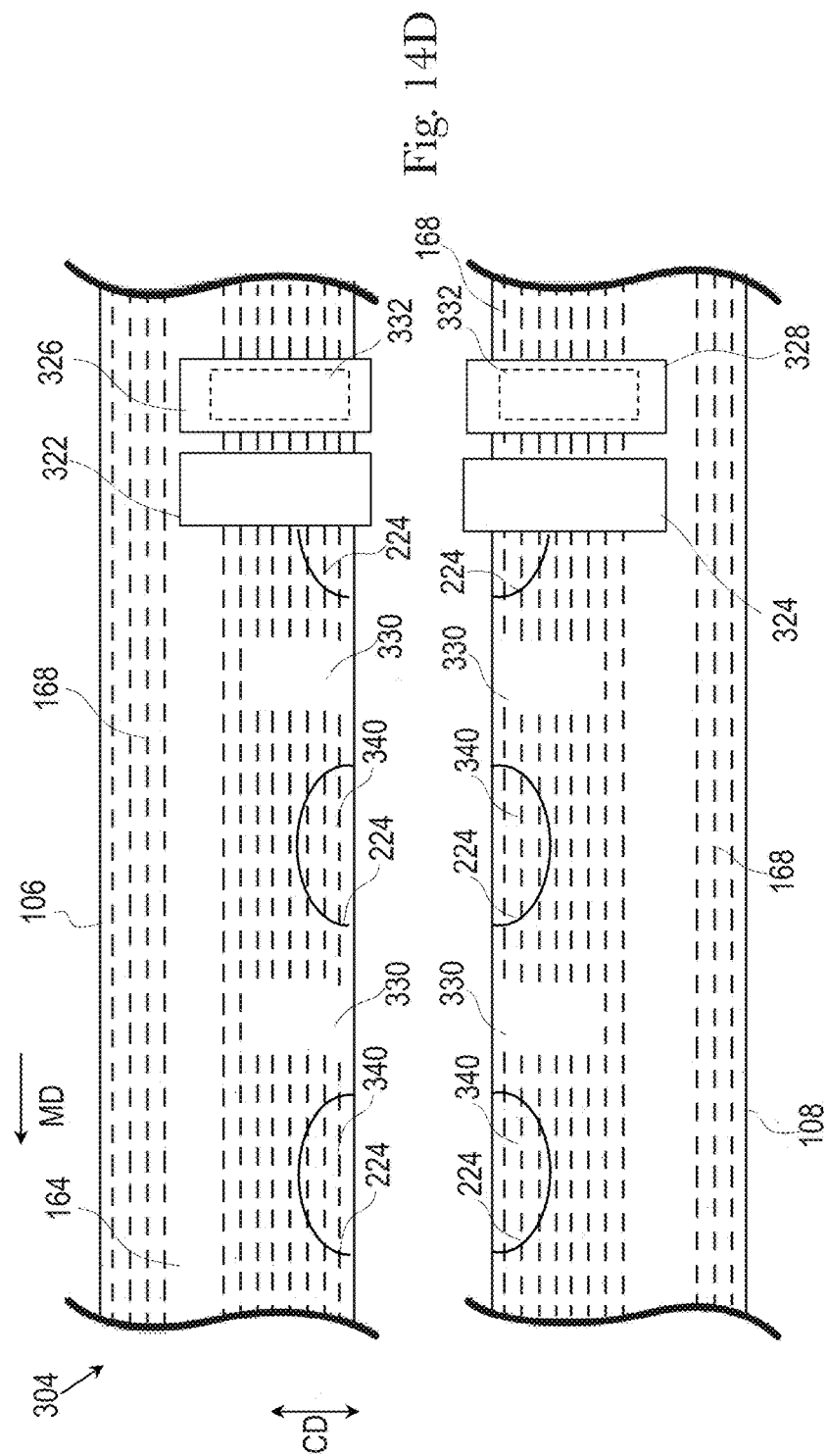
FIG. 14D is a top view of a belt assembly including a discrete line of weakness and a gap in accordance with one non-limiting embodiment of the present disclosure.

In some embodiments, a series of laser sources may be used, as illustrated in FIG. 14D. For example, a first laser source 322 may be used to impart a discrete line of weakness 224 into a first belt 106 and a second laser source 324 may be used to impart a discrete line of weakness 224 into a second belt 108. Further, a third laser source 326 and a fourth laser source 328 may be used to sever one or more elastic strands 168 in the belt assembly 304. More specifically, the third laser source 326 may be used to sever one or more elastic strands 168 in the first belt 106 and the fourth laser source 328 may be used to sever one or more elastic strands 168 in the second belt 108. The elastic strands 168 may be located in the portion of the belt assembly that overlaps a discrete component or sub-assembly, such as an absorbent core, as described with reference to FIGS. 2 and 4, which may be disposed on the belt assembly 304 in a subsequent process. The elastic strands 168 may be severed in this region to prevent the belt assembly from gathering in the region of the absorbent core and/or the chassis, which are examples of component parts that may be added to the belt assembly 304. The laser source may be configured to sever any number of elastics 168. Thus, the size of the gap 330 in the elastic stands 168 may differ across a belt assembly 304. For example, if the elastic strands 168 have been continuously bonded to the substrate, there may be no gap 330 or minimal gap 330 between severed elastic strands 168. Alternatively, if the elastic strands 168 have been intermittently bonded to the substrate, the severed elastic strands 168 may snap back to a portion of the elastic strand that has been bonded to the substrate forming a gap 330. Thus, the gap 330 may be of a uniform width or a non-uniform width. It is to be appreciated that a configuration of laser sources and their associated scan heads may also be present adjacent the opposite side of the substrate as set forth in FIG. 14D.

In some embodiments, the laser source may be operated in the cross direction as the belt assembly advances in the machine direction to sever the one or more elastic strands. More specifically, the laser source and/or the laser beam emitted by the laser source may be operated such that it imparts a continuous line across the portion of the elastic strands that are desired to be severed. It is to be appreciated that the laser source 312 and/or laser beam may also move in a direction at an angle to the cross direction CD. For example, the laser source 312 or laser beam may move in a substantially diagonal direction due to the movement of the belt assembly 304 in the machine direction MD. Thus, the movement of the belt assembly in the machine direction may be accounted for in the movement of the laser such that the laser source and/or laser beam moves in a diagonal direction so that the elastic strands are severed in a line extending parallel to the cross direction.

Figure 14E:
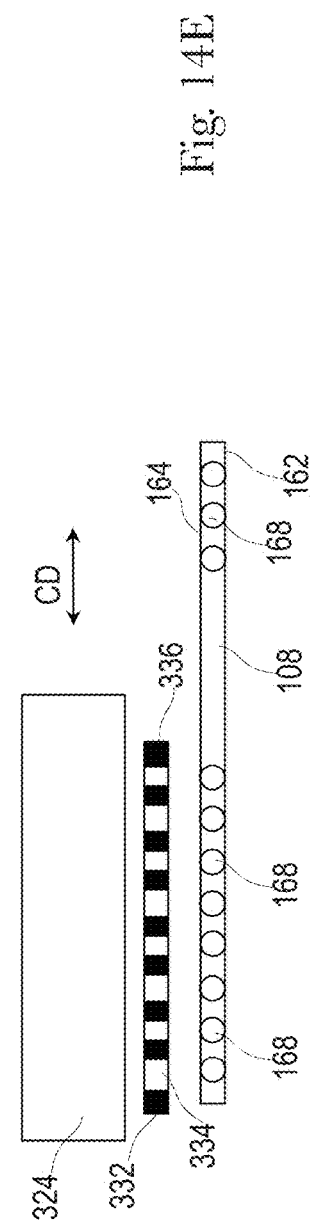
FIG. 14E is a schematic representation of a side view of a mask positioned between a laser source and a portion of the belt assembly disposed on a process member in accordance with one non-limiting embodiment of the present disclosure.

In some embodiments, a mask 332 may be used to prevent those portions of the nonwoven that do not overlap an elastic strand 168 from being affected by the laser source. The mask 332 may be positioned between the laser source 324 and the belt assembly 304, as illustrated in FIGS. 14D and 14E. The mask 332 may include transfer portions 334, which allows the laser source to interact with the substrate and the elastic strand(s), and preventative portions 336, which stops the laser source from acting on the substrate and the elastic strand(s). The mask 332 may be positioned such that the transfer portions 334 coincide with the elastic strands and the preventative portions 336 coincide with the portions of the elastic belt that do not have elastic strands. Stated another way, a laser source may continuously operate as it moves in the cross direction to sever the elastic strands 168. The mask allows the laser source to affect only certain portions of the nonwoven substrate(s), most desirably portions overlapping elastic strands 168. The mask 332 may be configured with any number of transfer portions and preventative portions. The number and design of these portions will depend, in part, on which portions of the nonwoven substrate(s) it is desirable for the laser source to affect. The mask may be moveable in the machine direction MD and the cross direction CD. The mask may be continually adjusted in one or more directions so that it may maintain alignment with the portion of the substrate that is desired to be acted on by the laser source.

In some embodiments, the laser source may be pulsed so that certain portions of the nonwoven substrate remain unaffected by the laser source. For example, the laser source may be controlled such that the laser source is powered on for a certain period of time and off for a certain period of time. The amount of the time the laser source is powered on and powered off may depend, in part, on the speed of the belt assembly advancing in the machine direction and the characteristics of the line of weakness. The amount of time that the laser source is powered on and powered off may be changed each time the laser source completes an on/off cycle. Thus, the laser source may remain powered on for a longer period of time in a first cycle and remain powered on for a shorter period of time in a subsequent cycle.

Pulsing of the laser source may also be used to impact the quality of the line of weakness or the cut. For example, pulsing the laser source may reduce the amount of heat transferred to the material in a region, thereby reducing the amount of melting of individual fibers and the clustering of adjacent fibers. Thus, pulsing may also aid in improving the softness, as perceived by the user, of the cut edge or separated edge.

Pulsing of the laser source may be used to impart both a continuous line of weakness or a discrete line of weakness. Pulsing of the laser source may result in the line of weakness having individual discrete segments of areas affected by the laser source. Thus, a discrete line of weakness may include discrete segments and a continuous line of weakness may include discrete segments when imparted by a laser source that has been pulsed.

It is to be appreciated that to use the laser source in this manner to sever one or more elastics, the location of the elastics must be known or detected. As previously described, the outer circumferential surface of the process member may include one or more grooves. Thus, each elastic strand may be disposed within a groove, or those elastic strands that are to be severed may be disposed within one or more grooves. The location of the grooves may be predetermined and, therefore, the location of the elastic strands may be known. Alternatively or in addition to the aforementioned, a high speed camera may be used to detect the position of the elastic strands. The position of the elastic strands may then be communicated to the laser source and the laser source may be operated accordingly.

FIG. 14F illustrates a first laser source 322 and a second laser source 324 adjacent the wearer facing surface 164 of a belt assembly 304 including a body substrate 316. In some embodiments, the first laser source 322 may be used to sever one or more elastic strands 168 to form a gap 330 in the elastic strands. To sever the one or more elastic strands 322, the first laser source may be pulsed, so that the laser source is powered on while it is disposed over an elastic strand and powered off while it is not disposed over an elastic strand. Alternatively, or in addition to pulsing the laser source, a mask may be used to control which portions of the substrate the laser source may affect. The pulsing of the laser source and the use of a mask may also be used in combination with an outer circumferential surface having one or more grooves to aid in locating the elastic strands that should be severed. A second laser source 324 may be used to impart a line of weakness. As illustrated in FIG. 14F, the second laser source 324 may impart a discrete line of weakness 224 into the body substrate 316. It is also to be appreciated that one or more continuous lines of weakness may also, or alternatively, be imparted into the body substrate 316 by the second laser source 324. The second laser source 324 may traverse in the cross direction CD to a second position. In the second position, the second laser source 324 may also be used to sever one or more elastic strands to form a gap 330 in the elastic strands. The one or more elastic strands 168 may be severed in any manner as previously discussed. It is to be appreciated that an additional configuration of laser source(s) and/or scan head(s) may be positioned adjacent the opposite, garment facing surface of the belt assembly to engage the garment facing surface as previously described with respect to the wearer facing surface.

It is to be appreciated that when severing the elastic strands, it is desirable to minimize the destruction by controlling the exposure of the substrate layers to the laser source and to ensure that the elastic strands are separated. Stated another way, the intent is to sever the elastic strand prior to separating all nonwoven fibers. Generally, the nonwoven substrate that is disposed between the laser source and the elastic strand will degrade, such as by melting and/or ablating, prior to the elastic strand due to the properties of the nonwoven substrate and the elastic strand. More specifically, each different material has a wavelength or range of wavelengths at which its absorptivity is greatest or optimal. Thus, a laser source may be chosen such that the wavelength emitted by the laser beam is more readily absorbed by the elastic strands than the nonwoven substrate. For example, a first laser source for cutting the elastic strands may operate at a wavelength from about 9.0 µm to about 9.6 µm and a second laser source for cutting and/or imparting a line of weakness to the substrate may operate at a wavelength from about 10.2 µm to about 10.6 µm. In this case, the elastic strands may break prior to all the fibers of the nonwoven substrate separating. It is to be appreciated that the elastic strands may be under tension when they are acted on by the laser source. Elastics under tension want to relax. This property of the elastic strands may also aid in cutting the elastic strand prior to breaking or separating all the fibers of the nonwoven substrate.

However, materials may be altered to increase their absorptivity even if the laser source is operating outside their optimal range of wavelengths. In some embodiments, the elastic strands may be chemically altered such that the elastic strands have an increased rate of energy absorption, or absorptivity. These chemical additives may be added to the material that forms each elastic strand prior to the elastic strand being formed, such as by extrusion or other known methods. These chemicals additives may also be added to the elastic strand after formation. For example, these chemicals may be applied topically to each elastic strand. These chemical additives may also be added to the adhesive that attaches the elastic strand to the nonwoven substrate. Such chemical additives are available from Clearweld, Binghamton, N.Y. These chemical additives may be added to ensure that the elastic strands 168 present in a line of weakness get severed or can be severed by a relatively low force upon separation of the trim from the belt assembly 304, and to ensure that the elastic strands 168 present in the region of the belt assembly 304 are severed while not destroying the substrate layers.

It is also to be appreciated that any number of laser sources may be used to either weaken or sever the elastic strands and/or to impart a continuous or discontinuous line of weakness into the belt assembly. For example, a single laser source may be used to impart a continuous or discontinuous line of weakness into the first and second belts 106, 108 and another laser source may be used to sever the elastic strands in both the first and second belts 106, 108.

A laser source may be any apparatus that produces and amplifies light, referred to herein as a laser beam. More specifically, a laser source may be any apparatus that transforms energy into other forms of electromagnetic radiation, for example light. In some embodiments, the laser source may be a $CO_2$ laser or a Nd:YAG laser. However, any type of laser that is capable of weakening a substrate may be used. A laser source may emit many hundreds of watts which can be concentrated over a relatively small area, also referred to as a focal area, which is determined, in part, by the spot size diameter. For example, the spot size diameter may be from about 5 µm to about 300 µm, and/or from about 50 µm to about 200 µm, and/or from about 100 µm to about 150 µm, including all 0.1 µm therebetween. It is to be appreciated that focal area is also dependent on the wavelength of the laser beam. However, if a laser source emits too much power, the one or more substrate layers may be cut or severed. The minimum power required to cut a substrate is referred to as a cutting power. It is to be appreciated that the cutting power is a value which is established based on the type of laser source, the properties of the belt assembly or other substrate(s), and operating parameters such as the speed of the substrate/belt assembly, the speed at which the laser beam is moved with respect to the substrate, and the focal area. By operating the laser source at less than its cutting power, a line of weakness may be imparted to the substrate. More specifically, to impart a line of weakness, a laser source may be operated from about 98% to about 5% of its cutting power.

For example, a laser source having a total power capacity of 600 watts may act on a belt assembly 304 including a first belt 106 including a first substrate, a second substrate, and elastic strands therebetween, as shown in FIG. 12A. If the laser source 312 having total power capacity of 600 watts is operated at a power of 100%-60% of its total power capacity, the laser source 312 cuts or severs the first belt 106. More specifically, if the total power capacity of the laser source 312 was 600 watts, the laser source 312 would emit 360 watts if it were operating at 60%. A laser source 312 emitting 360 watts cuts or severs the first belt 106. However, below 360 watts, the laser source 312 fails to cut through the first belt. Thus, the laser source has a cutting power of 360 watts. To impart a line of weakness, such as previously disclosed, the laser source 312 operates below 60% of the total power capacity or below 360 watts to impart a line of weakness rather than to cut or sever the belt. The laser source 312 may operate from about 59% to about 24% of its total power capacity, or, stated another way, the laser source may operate below about 99% of its cutting power. In this example, the laser source 312 may emit from about 330 watts to about 150 watts to impart a line of weakness into the belt 106. It is to be appreciated that the aforementioned is an example and factors such as the type of laser source, properties of the belt assembly, operating parameters of the laser source, as previously discussed, may affect the cutting power.

Generally, the lower the power emitted by the laser source the fewer the number of separated fibers. The optimal operating settings of the laser source 312 may be such that the laser source does not separate all the fibers present in the nonwoven substrates of the belt assembly 304. The precise settings of the laser source 312 may be dependent, in part, upon the materials into which the laser source is to impart the line of weakness, the type of laser source, and the distance of the laser source from the material or substrate. The aforementioned applies to any laser source discussed herein.

Upon the belt assembly 304 including at least one of a first discrete line of weakness and a continuous line of weakness and at least one of a second discrete line of weakness and a continuous line of weakness, the belt assembly 304 may continue to be advanced by the second guide roller 314. Referring to FIG. 11, the belt assembly 304 may be disposed about a portion of the second guide roller 314 and advanced toward subsequent processes. The second guide roller 314 may include a pressure source (not shown) that transfers a gas and/or fluid through the one or more apertures 318 causing the belt assembly 304 to be forced away from the outer circumferential surface 308 of the of the second guide roller 314.

FIGS. 15A and 15B illustrate another configuration of the guide rollers and their interaction with the belt assembly 304, the laser sources and their respective scan heads may operate as discussed with respect to FIGS. 11A and 11B.

Figure 15D:
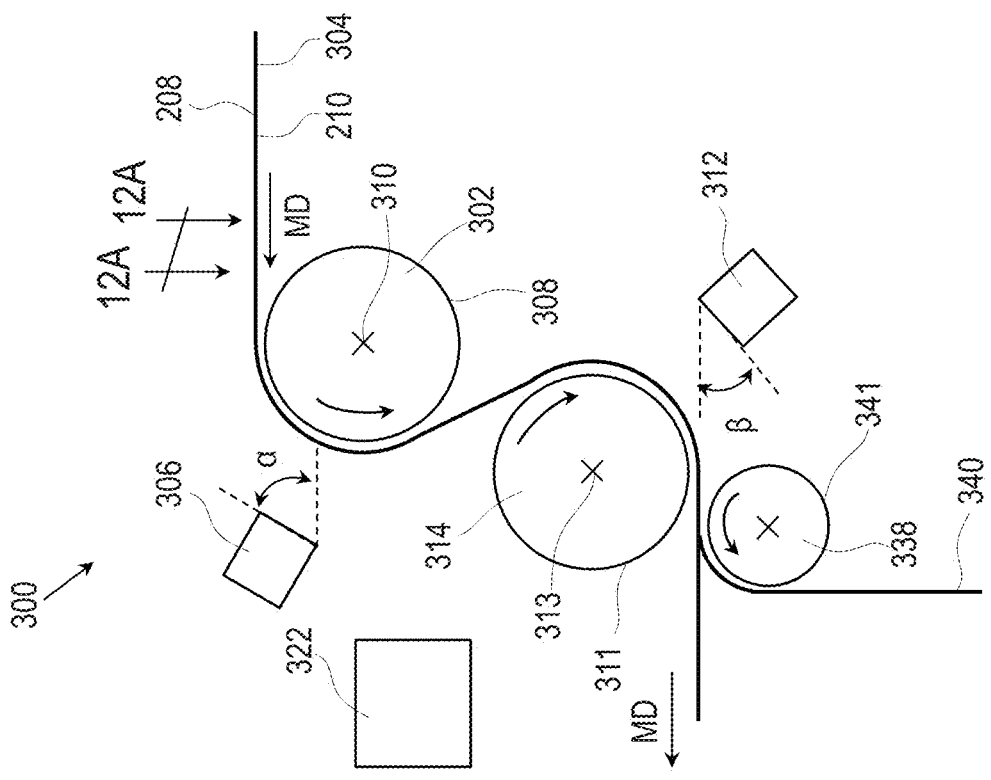
FIG. 15D is a schematic representation of an apparatus that imparts a first line of weakness into a first surface of a first substrate and a second line of weakness into a second surface of a second substrate in accordance with one non-limiting embodiment of the present disclosure.
Figure 15C:
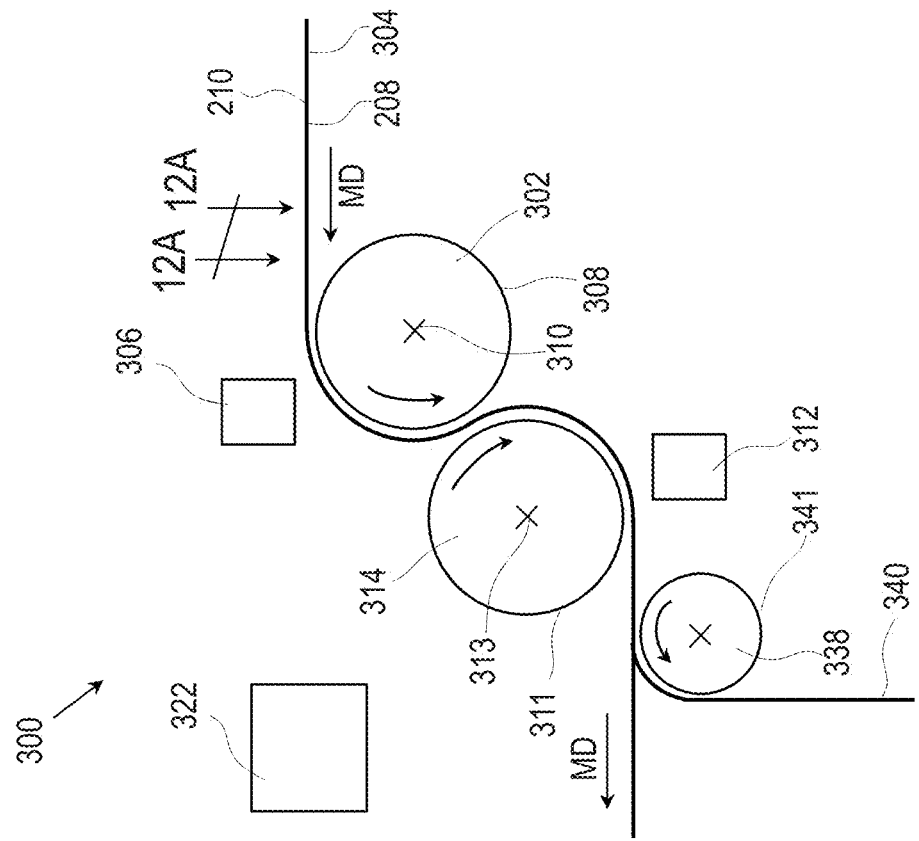
FIG. 15C is a schematic representation of an apparatus that imparts a first line of weakness into a first surface of a first substrate and a second line of weakness into a second surface of a second substrate in accordance with one non-limiting embodiment of the present disclosure.

During processing of the belt assembly 304, the first guide roller 302 and the second guide roller 314 may be positioned adjacent one another, as illustrated in FIGS. 15C and 15D. This configuration may be referred to herein as an s-wrap configuration. The first guide roller 302 and the second guide roller 314 may be positioned such that the outer circumferential surface 308 of the first guide roller 302 is parallel to or in an overlapping relationship with a portion of the outer circumferential surface 311 of the second guide roller 314 as illustrated in FIGS. 15C and 15D. Stated another way, the distance measured parallel to the machine direction MD between the first axis of rotation 310 of the first guide roller 302 and the second axis of rotation 313 of the second guide roller 314 may be equal to or less than the sum of the radius of the first guide roller 302 and the radius of the second guide roller 314. Either the first surface 208 or the second surface 210 may be disposed about each of the first guide roller 302 and the second guide roller 314.

For example, as illustrated in FIG. 15C, the belt assembly 304 may be configured such that the first surface 208 is disposed about the outer circumferential surface 308 of the first guide roller 302 and the second surface 210 is disposed about the outer circumferential surface 310 of the second guide roller 314. Thus, as the first surface 208 is disposed on the outer circumferential surface 308 of the first guide roller 302, the first laser source 322 may emit a laser beam such that the laser beam operatively engages a first scan head 306. The first scan head 306 directs the laser beam at the second surface 210 and may impart a first line of weakness into the second surface 210. The belt assembly 304 may continue to advance in the machine direction MD such that the second surface 210 is disposed on the outer circumferential surface 311 of the second guide roller 314. Thus, as the second surface 210 is disposed on the outer circumferential surface 311 of the second guide roller 314, the first laser source 322 may emit a laser beam such that the laser beam operatively engages a second scan head 312. The second scan head 312 directs the laser beam at the first surface 208 and may impart a second line of weakness into the first surface 208. The first line of weakness and the second line of weakness are coincident, as previously discussed.

As illustrated in FIG. 15D, it is to be appreciated that the first guide roller 302 and the second guide roller 314 may be positioned in a s-wrap configuration and the belt assembly 304 may traverse this configuration such that there is an unsupported portion of the belt assembly 304 as the belt assembly 304 advances from the first guide roller 302 to the second guide roller 314. Thus, the laser beam may affect the portion of the belt assembly disposed on the outer circumferential surface of the guide roller and/or the unsupported portion of the belt assembly.

Further, as the belt assembly 304 is transferred from the second guide roller 314, the belt assembly may engage a trim removal member 338, as illustrated in FIGS. 15C and 15D. The trim removal member 338 may be configured to engage the trim 340, or the portion along the first line of weakness and the second line of weakness that is to be removed from the belt assembly. The trim 340 may be disposed about a portion of the outer circumferential surface 341 of the trim member 338 while the remainder of the belt assembly 304 is advanced to other downstream processes. The trim 340 may be removed immediately after the first and second line of weakness are imparted to the belt assembly or the trim 340 may remain attached during subsequent processing and removed after several other processes have been performed on the belt assembly.

It is also to be appreciated that one or more additional devices such as a cutting device including a blade, an additional laser source, or another roller may be used to aid in the removal of the trim 340 from the belt assembly 304.

Figure 16:
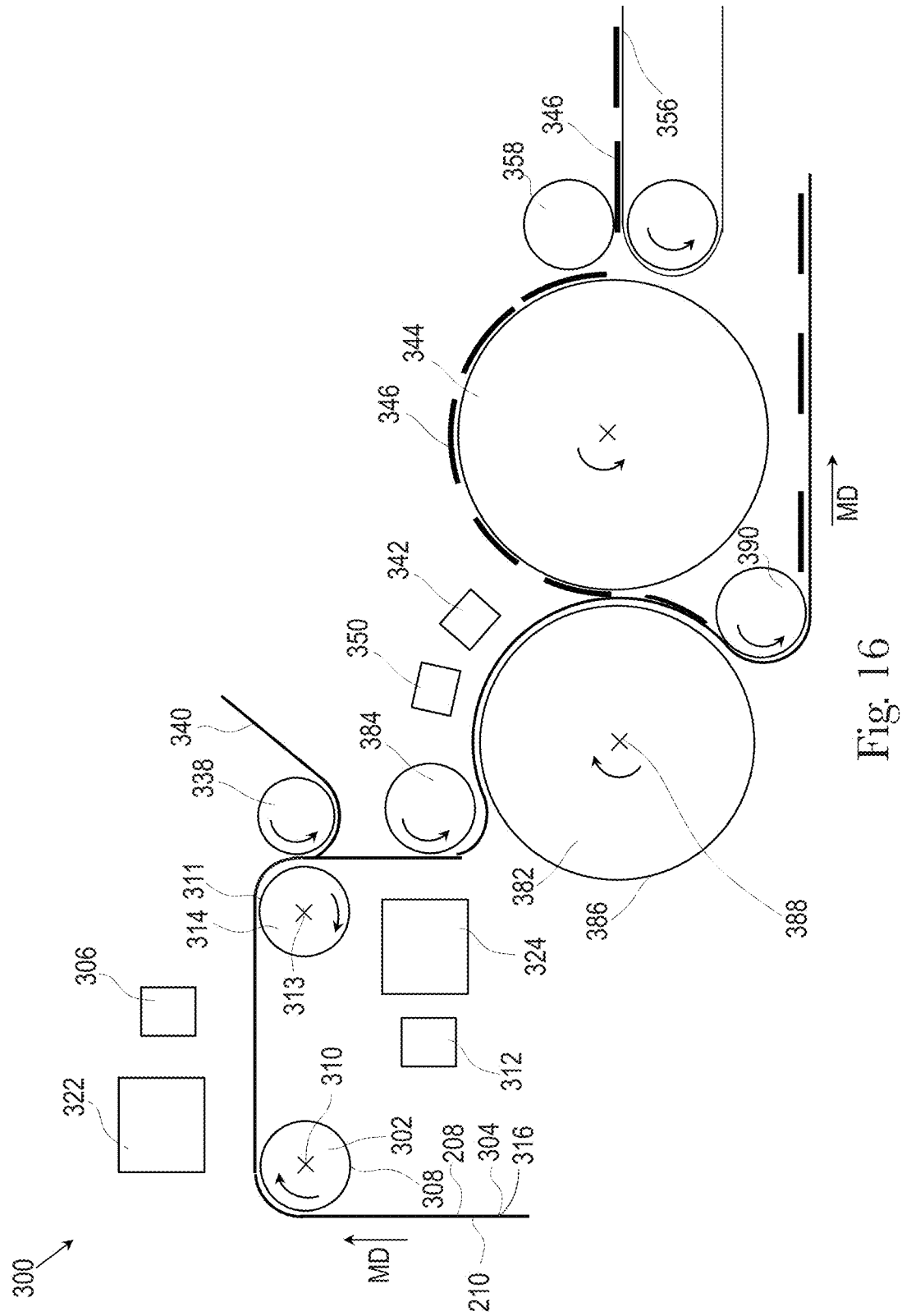
FIG. 16 is a schematic representation of an apparatus that imparts a first and second line of weakness into a first and second substrate and a process member for performing other processed on the first and second substrates in accordance with one non-limiting embodiment of the present disclosure.

As previously discussed, the belt assembly 304 may undergo one or more processes. FIG. 16 illustrates an example embodiment of an apparatus 300 that may be used to manufacture an absorbent article 100. The belt assembly 304 may advance such that belt assembly 304 is disposed on a portion of a first roller guide 302 and a second roller guide 314 and the belt assembly is acted on by a first laser beam and a second laser beam to impart a first line of weakness and a second line of weakness, as previously discussed.

Figure 17A:
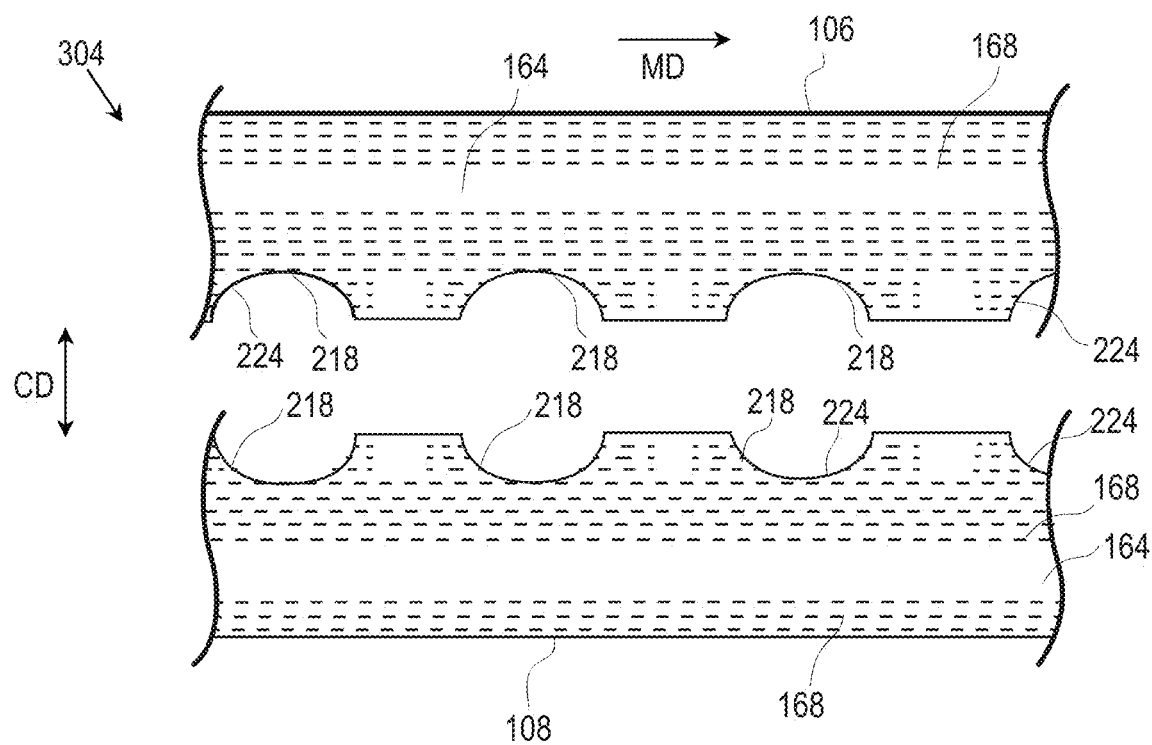
FIG. 17A is a top view of a belt assembly including a discrete separation edge in accordance with one non-limiting embodiment of the present disclosure.
Figure 17B:
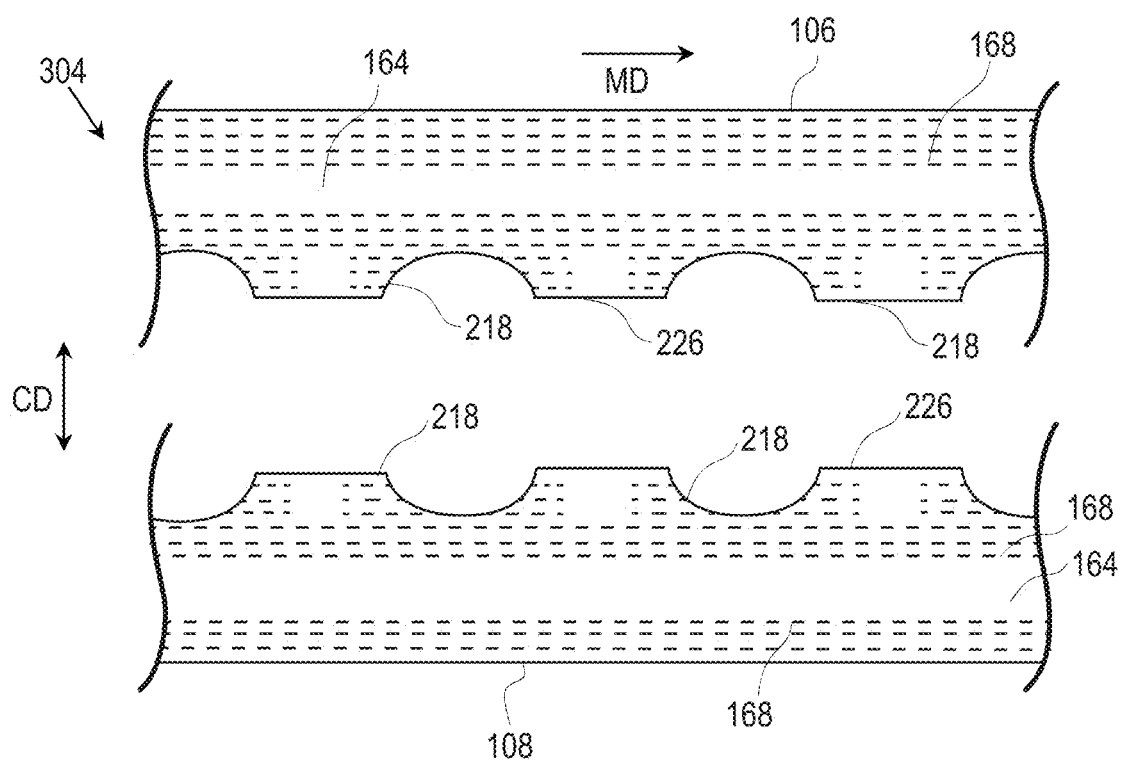
FIG. 17B is a top view of a belt assembly including a continuous separation edge in accordance with one non-limiting embodiment of the present disclosure.

The belt assembly 304 having a first line of weakness and a second line of weakness, and each of the first line of weakness and the second line of weakness including at least one of a continuous line of weakness and a discrete line of weakness, may advance to a trim removal member 338. The trim removal member 338 may remove the trim 340, which may include a discrete portion and/or a continuous portion of the line of weakness, as illustrated in FIGS. 14B and 14C. A trim removal member 338 may apply a force to the discrete or continuous line of weakness to remove continuous lengths of trim as well as discrete pieces of trim that have been weakened by the laser source 312. More particularly, as the first belt 106 and the second belt 108 advances in the machine direction, the trim removal member 338 may be used to separate and remove trim from and/or along either or both opposing side edges of the first belt 106 and the second belt 108. The trim removal member 338 may include an apparatus such as disclosed in U.S. Publ. No. 2012/0079926. Other devices that may be suitable as a trim removal member 338 include a vacuum head including one or more vacuum nozzles, which may be used to separate the trim 340 from the belt assembly, and a duct system, which may be used to transport the trim from the process member to a disposal location. FIGS. 17A-17B illustrate the belt assembly 304 upon removal of the trim 340. Upon removal of the trim 340 a separation edge 218 is formed, such as previously discussed with reference to FIGS. 8, 9A-9B, and 10A-10B. It is to be appreciated that another device may be used in the removal of trim 340 such as cutting device including a blade, a pressure roller, a hot air supply device, and/or another laser source.

The belt assembly 304 may advance in a machine direction MD toward the process member 382. A fourth guide roller 384 may aid in the transfer of the belt assembly 304 onto an outer circumferential surface 386 of the process member 382. The outer circumferential surface 386 of the process member 382 may include one or more apertures. A vacuum source, not shown, may be in fluid communication with the one or more apertures. The vacuum source allows a gas to be circulated through the one or more apertures toward the longitudinal axis of rotation 388. The movement of fluid may result in the belt assembly 304 being forced toward the outer circumferential surface 386 of the process member 382. The process member 382 may rotate about the longitudinal axis of rotation 388 causing the belt assembly 304 to advance toward one or more processes. For example, the process member 382 may then advance the belt assembly 304 to a cutting member 350. The cutting member 350 may be used to sever one or more elastic strands 168 or any other portion of the belt assembly 304. The cutting member 350 may be an apparatus such as disclosed in U.S. Pat. No. 8,440,043. The cutting member 350 may also be a laser.

The belt assembly 304 may then be advanced to an adhesive applicator 342. The adhesive applicator may apply adhesive, such as glue, to the belt assembly 304. The adhesive may be applied to a portion of the first belt 106 and a portion of the second belt 108. The adhesive may be applied to portions of the first belt 106 and the second belt 108 where additional components of the absorbent article are to be added. For example, the adhesive may be applied to the portion of the belt assembly 304 having severed elastic strands 168.

Upon applying adhesive to the belt assembly 304, the belt assembly 304 may be advanced to operatively engage with a transfer member 344. The transfer member 344 may be used to transfer and/or rotate a discrete component 346 of the absorbent article. An example of a discrete component 346 is a chassis 102, such as discussed with reference to FIGS. 2 and 4. In some embodiments, the transfer member 344 may receive a discrete component 346 positioned in a first orientation 352, as illustrated in FIG. 18A. More specifically, the discrete component 346 may be orientated in a first orientation 352 when the longitudinal axis 124 of the discrete component 346 is substantially parallel to the machine direction MD and/or substantially perpendicular to the cross direction CD. However, to be disposed on the belt assembly 304, the discrete component 346 may need to be rotated. In the embodiments wherein the discrete component 346 is a chassis 102, the chassis 102 may need to be rotated so that a first portion of the chassis 102 is disposed on the first belt 106 and a second portion of the chassis 102 is disposed on the second belt 108. Thus, the transfer member 344 may be configured to transfer the discrete component 346 from a first carrier member 356, which may include a conveyor belt supported by one or more guide rollers. A third guide roller 358 may be used to aid in transferring the discrete component 346 onto the outer circumferential surface 360 of the transfer member 344 from the carrier member 356. The transfer member 344 may advance the discrete component 346 to a position that allows the discrete component 346 to be disposed on a portion of the belt assembly 304. In some embodiments, the transfer member 344 may also rotate the discrete component to a second orientation 354, as illustrated in FIG. 18B. More specifically, the discrete component 346 may be orientated in a second orientation 352 when the longitudinal axis 124 of the discrete component 346 is substantially perpendicular to the machine direction MD and/or substantially parallel to the cross direction CD. It is to be appreciated that the discrete component 346 may not be rotated or may be rotated in any position that allows the discrete component 346 to be orientated in a desired position. The transfer member 344 may be an apparatus such as that disclosed in U.S. Pat. No. 8,820,513.

As illustrated in FIG. 16, the transfer member 344 may be operatively engaged with the process member 382. More specifically, as the belt assembly 304 rotates about the longitudinal axis of rotation 388, the transfer member 344 may transfer a discrete component 346 onto at least a portion of the belt assembly 304. In some embodiments, as illustrated in FIG. 18C, the transfer member 344 may transfer a chassis 102 onto a portion of the first belt 106 and a portion of the second belt 108. Stated another way, a first portion of the chassis 102 may be disposed on a portion of the first belt 106 and a second portion of the chassis 102 may be disposed on the portion of the second belt 108. As was previously discussed, an adhesive may be applied to the belt assembly 304. The adhesive may allow the chassis 102 to be adhered to the belt assembly 304, and, thus, be transferred from the transfer member 344 to the process member 382.

Still referring to FIG. 16, the belt assembly 304 including the discrete component 346, such as a chassis 346, may be advanced by the process member 302 to a fifth guide roller 390. The fifth guide roll 390 may be used to transfer the belt assembly 304 including the discrete component 346 to additional downstream processes. In some embodiments, the fifth guide roller 390 may also act as a bonding roll. The fifth guide roller 390 may be positioned such that pressure is applied to the belt assembly 304 and the discrete component 346 as the combination passes between the fifth guide roller 390 and the process member 382. The fifth guide roller 390 may be used to bond the discrete component 346 to the belt assembly 304.

Figure 19:
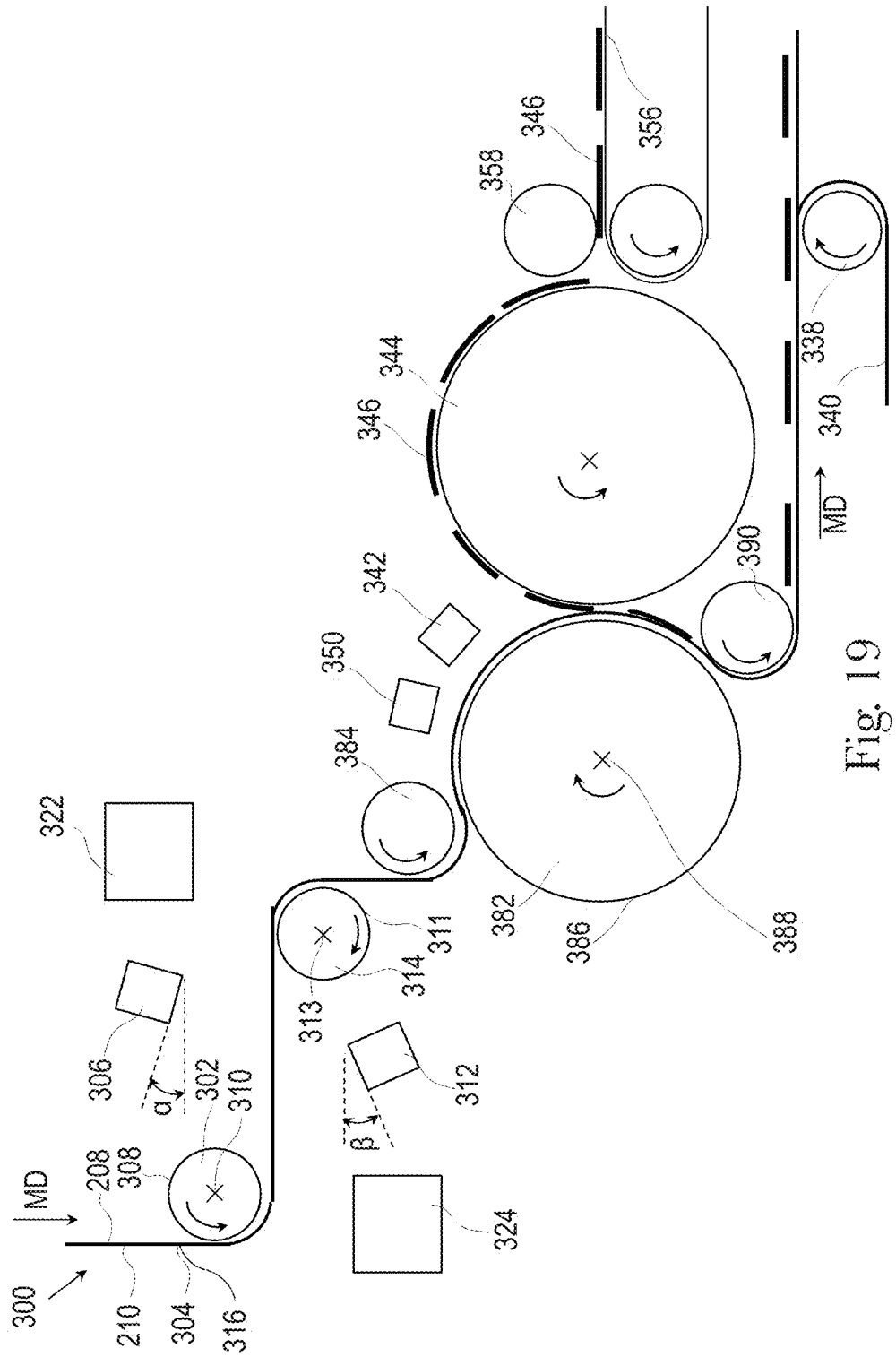
FIG. 19 is a schematic representation of an apparatus that imparts a first and second line of weakness into a first and second substrate and a process member for performing other processed on the first and second substrates in accordance with one non-limiting embodiment of the present disclosure.

FIG. 19 illustrates embodiments wherein a discrete component 346 may be disposed on the belt assembly 304 prior to the trim 340 being removed from the belt assembly 304. More specifically, the belt assembly 304 may be acted upon such that a first line of weakness and a second line of weakness, coincident with the first line of weakness, is imparted to the belt assembly 304. Further, one or more discrete components 346 may be disposed on the belt assembly 304. Subsequently, the belt assembly 304 may be advanced such that a trim removal member 338 engages the belt assembly 304 causing the discrete and/or continuous trim 340 to engage with the outer circumferential surface of the trim member 338 and for the remainder of the belt assembly 304 including the discrete component 346 to advance in a machine direction MD away from the trim member 338. As previously discussed, the trim removal member 338 may be an apparatus such as disclosed in U.S. Publ. No. 2012/0079926. It is to be appreciated that the first line of weakness and the second line of weakness may be strong enough to hold the trim 340, or the portion of the belt assembly that is to be removed, together with the remainder of the belt assembly during subsequent process. Thus, the trim 340 remains attached until acted upon by the trim member 338. However, the first and second lines of weakness may also be weak enough that the trim 340 is separated when acted upon by the trim member 338 and/or any additional devices that may aid in separating the trim 340.

Although much of the present disclosure is provided in the context of manufacturing absorbent articles, it is to be appreciated that the apparatuses and methods disclosed herein may be applied to the manufacture of other types of articles and products manufactured from continuous substrates. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, pre-moistened cloths, paper towels, dryer sheets and dry-cleaning clothes such. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, training and pull-on pants, adult incontinence briefs and undergarments, feminine hygiene garments such as panty liners, absorbent inserts, and the like, toilet paper, tissue paper, facial wipes or clothes, and toilet training wipes. Still other examples of products may include packaging components and substrates and/or containers for laundry detergent, which may be produced in pellets or pouches and may be manufactured in a converting or web process or even discreet products produced at high speed such as high-speed bottling lines, cosmetics, razor blade cartridges, and disposable consumer batteries.

It is also to be appreciated that the separation edge 218 and/or the cut edge 202 may be softened mechanically after being acted on by the laser source. The accumulated material or clusters of accumulated material lead to the edge feeling rough or sharp. Generally, the skin perceives a nonwoven edge as soft if the end of fibers produces a small amplitude wave and little periodicity. The skin perceives an edge as rough if the amplitude and periodicity of the wave produced between the skin and fiber ends is other than flat. The higher the amplitude and the shorter the period, the rougher the edge feels.

The laser source ablated a portion of the individual fiber ends and melted the individual fiber ends that were in proximity to the ablated portion. Thus, the individual fibers that underwent melting include an accumulation of material at the tip, also referred to as a sphere of material. This sphere of material may be three to four times the diameter of the individual fiber that did not undergo melting or was not ablated.

The size of the individual fibers that have undergone melting may be increased as they are joined together. For example, a medium size cluster may be formed by more than two fiber-ends melted together. This medium size cluster forms a larger sphere having a diameter greater than three times or greater than about four times the diameter of an individual fiber diameter. Clusters of material form a linear, seemingly high density edge, at least as thick as the nonwoven composite caliper. Thus, it is important that these clusters may be broken up before use in an absorbent article.

In some embodiments, the separation edge or the cut edge may be fed through two rollers. The two rollers exert pressure on the edge causing the edge to be strained. The straining of the edge breaks up some of these clusters of accumulated material resulting in a relatively softer feeling edge. The material of the surface of the rollers may be important to induce the required strain on the edge to remove the clusters. It is also to be appreciated that the material may be chosen such that the elastic strands that are fed between the nip of the two rollers do not get damaged in the process of straining the edge. For example, a first roller may have a metal surface and a second roller may have a rubber surface. Further, the first roller may have a substantially smooth surface or the first roller may have a patterned surface.

In some embodiments, the edge may be activated, such as by ring rolling as disclosed in U.S. Pat. No. 4,116,892, or by plate activation as disclosed in U.S. Pat. No. 6,500,377. Activating the edge may also reduce the rough or sharp feeling of the edge due to breaking up the clusters of accumulated material. The amount of cluster break up during this process may be due in part to the tooth tip radius, the distance between adjacent teeth, the tooth height, the tooth wall angle, the temperature, and depth of tooth engagement.

Figure 20:
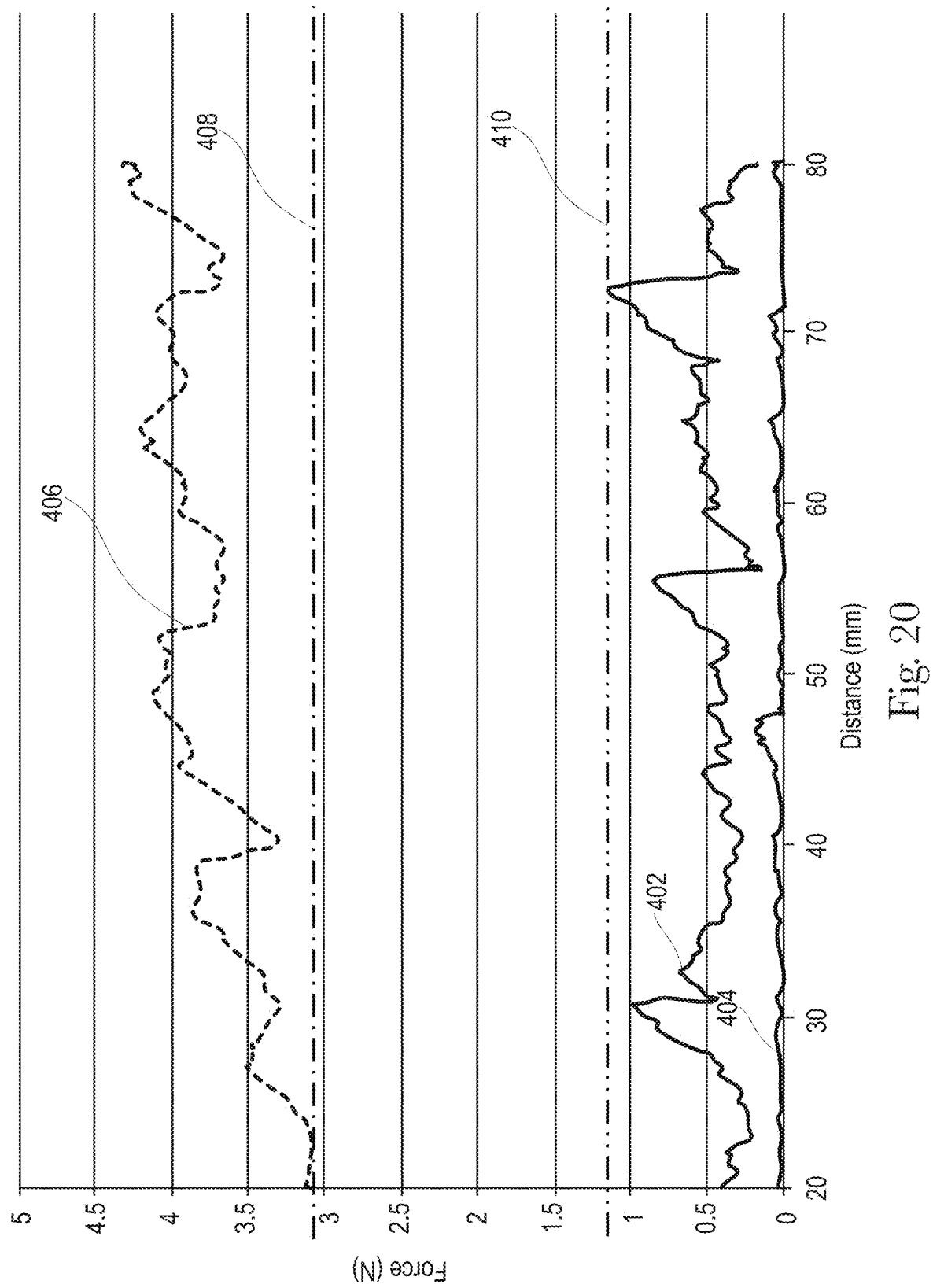
FIG. 20 is a graphical illustration of the force required to separate a laminate in accordance with one non-limiting embodiment of the present disclosure.

As previously discussed, the line of weakness imparted to the substrate requires subsequent separation. The force required to separate the substrate along the line of weakness depends, in part, on the characteristics of the line of weakness. Generally, the greater the number of fibers severed by the laser source, the easier the substrate will be to separate along the line of weakness. FIG. 20 illustrates this concept.

FIG. 20 illustrates the separation force required to separate a laminate with and without a line of weakness. More specifically, a $CO_2$ type laser source having a total power capacity of 600 watts was used to impart a line of weakness into a laminate. The laminate included two substrate layers. Each of the substrate layers were made from spunbond polypropylene to from a nonwoven and each layer had a basis weight of about 20 gsm. The two substrate layers were held together with a construction adhesive, such as Dispomelt 526, having a basis weight of 6 gsm. The laminate was passed through the laser source at a speed of about 500 m/min and the spot size diameter of the laser beam being emitted by the laser source was 140 µm. The laser source was used to impart a first line of weakness into a first laminate. To impart the first line of weakness, the laser source emitted a power output of about 180 watts. The laser source was then used to impart a second line of weakness into a second laminate. To impart the second line of weakness, the laser source emitted a power output of 270 watts. A first separation force 402 was applied to the first laminate to separate the first line of weakness. The change in the first separation force 402 as the first laminate was separated along the first line of weakness is illustrated in FIG. 20. A second separation force 404 was applied to the second laminate to separate the second line of weakness. The change in the second separation force 404 as the second laminate was separated along the second line of weakness is also illustrated in FIG. 20. For purposes of comparison, a third separation force 406 was applied to a third laminate that was not acted on by the laser source and, thus, did not include a line of weakness. The change in the third separation force 406 as the third laminate was separated is also illustrated in FIG. 20.

As shown in FIG. 20, imparting a line of weakness into the laminate reduces the amount of force required to separate a laminate. Further, by increasing the power of the laser source, the amount of force required to separate the laminate along the line of weakness was reduced. However, it is to be appreciated that by increasing the power of the laser source, the accumulated material and/or clusters along the separation edge may increase. The optimal characteristics of the line of weakness imparted to a substrate may depend, in part, on the force required to separate the substrate along the line of weakness and the characteristics of the separation edge.

The line of weakness imparted to the laminate or other substrate(s) may be such that the force required to separate the laminate or other substrate(s) is less than the force required to separate the laminate or other substrate(s) that have no line of weakness. For example, as illustrated in FIG. 20, a third separation force 406 was required to separate the third laminate, and the third laminate included no line of weakness. The lowest point on the third separation force 406 curve is illustrated within minimum force line 408. It is to be appreciated that the separation force required to separate any line of weakness imparted to a laminate or other substrate(s) be below the minimum force line for that particular laminate or substrate(s). For example, as illustrated in FIG. 20, for the second laminate, the second separation force 404 was plotted as the line of weakness imparted to the second laminate was separated. This second separation force 404 includes a maximum force line 410, which intersects the greatest force required during the separation of the second laminate. As illustrated, the maximum force line 410 is below or less than the minimum force line 408.

If the maximum force line 410 was above or greater than the minimum force line 410, this may be evidence that the substrate(s) or laminate has separated in an area other than the line of weakness. The line of weakness may be used to control where the substrate(s) or laminate separate. Further, this may be evidence that the laser source is improper for the given substrate(s) or laminate. For example, the laser source is not strong enough to impart a proper line of weakness into the substrate(s) or laminate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing an absorbent article, the method comprising:
    advancing a belt assembly, wherein the belt assembly comprises a first substrate defining a first outer surface, a second substrate defining a second outer surface, and an elastic material disposed between the first substrate and the second substrate; and
    advancing the belt assembly to a first laser assembly, where the first laser assembly comprises a first laser source positioned adjacent the first surface and a second laser source positioned adjacent the second surface, wherein the first laser source operatively engages the first surface of the belt assembly imparting a first line of weakness on the first surface of the belt assembly and the second laser source operatively engages that second surface of the belt assembly imparting a second line of weakness on the second surface of the belt assembly, wherein the first line of weakness and the second line of weakness are coincident.

2. The method of claim 1, wherein the elastic material comprises one or more elastic strands disposed between the first substrate and the second substrate.

3. The method of claim 2, further comprising the step of advancing the belt assembly to a third laser source, wherein the third laser source severs a portion of the one or more elastic strands forming a gap in the one or more elastic strands.

4. The method of claim 1, further comprising the steps of:
    advancing a discrete component on a carrier member;
    rotating a transfer member about a first axis of rotation, wherein the transfer member comprises a substantially flat transfer surface;
    accepting the discrete component on the substantially flat transfer surface; and
    positioning the discrete component on a portion of the belt assembly.

5. The method of claim 1, wherein at least one of the first line of weakness and the second line of weakness includes one or more discrete lines of weakness.

6. The method of claim 1, wherein at least one of the first line of weakness and the second line of weakness is a continuous line of weakness.

7. The method of claim 1, further comprising the step of advancing the belt assembly around a portion of a first guide roller, wherein the first guide roller comprises a first outer circumferential surface and is configured to rotate about a first axis of rotation, and wherein the first guide roller is positioned upstream in a machine direction of the laser assembly.

8. The method of claim 7, further comprising the step of advancing the belt assembly around a portion of a second guide roller, wherein the second guide roller comprises a second outer circumferential surface and is configured to rotate about a second axis of rotation, and wherein the second guide roller is positioned downstream in a machine direction of the laser assembly.

9. The method of claim 8, wherein at least one of the first outer circumferential surface and the second outer circumferential surface comprise one or more grooves.

10. The method of claim 8, wherein the first surface of the belt assembly is disposed on the first outer circumferential surface and the second outer circumferential surface.

11. The method of claim 8, wherein the first surface of the belt assembly is disposed on the first outer circumferential surface and the second surface of the belt assembly is disposed on the second outer circumferential surface.

12. The method of claim 1, further comprising the step of advancing the belt assembly to a trim removal member, wherein the trim removal member removes trim from the first and second lines of weakness forming a separation edge.

13. The method of claim 1, wherein the first laser source emits a first laser beam configured to engage a first scan head and the second laser source emits a second laser beam configured to engage a second scan head, and wherein the first scan head is at an angle to the second scan head.

14. The method of claim 13, wherein the first scan head is offset from the second scan head.

15. The method of claim 1, wherein the first laser source emits a first laser beam configured to engage a first scan head and the second laser source emits a second laser beam configured to engage a second scan head, and wherein the first scan head is parallel to the second scan head.

16. A method for manufacturing an absorbent article, the method comprising:
   rotating a first guide roller about a first axis of rotation;
   rotating a second guide roller about a second axis of rotation, wherein the first guide roller is adjacent the second guide roller;
   advancing a belt assembly around a portion of the first guide roller, wherein the belt assembly comprises a first substrate, a second substrate, and an elastic material disposed therebetween;
   disposing the second substrate of the belt assembly on an outer circumferential surface of the first guide roller;
   advancing the belt assembly to a first laser beam, wherein the first laser beam imparts a first line of weakness into the first substrate;
   advancing the substrate assembly between the first guide roller and the second guide roller;
   disposing the first substrate of the belt assembly on an outer circumferential surface of the second guide roller; and
   advancing the belt assembly to a second laser beam, wherein the second laser beam imparts a second line of weakness into the second substrate, wherein the second line of weakness is coincident with the first line of weakness.

17. The method of claim 16, further comprising the step of advancing the belt assembly to a trim removal member, wherein the trim removal member separates the line of weakness forming a trim portion and a separation edge.

18. The method of claim 16, wherein the elastic material comprises one or more elastic strands disposed between the first substrate and the second substrate.

19. The method of claim 16, wherein the belt assembly comprises a first belt and a second belt.

20. The method of claim 16, wherein the belt assembly comprises a body substrate.

21. The method of claim 16, wherein the first laser beam is emitted by a first laser source and the second laser beam is emitted by a second laser source.

22. The method of claim 16, wherein the first laser beam operatively engages a first scan head and the second laser beam operatively engages a second scan head.

23. A method for manufacturing an absorbent article, the method comprising:
   advancing a belt assembly around a portion of a first guide roller, wherein the belt assembly comprises a first substrate defining a first outer surface and a second substrate defining a second outer surface;
   advancing the belt assembly around a portion of a second guide roller, wherein an unsupported portion of the belt assembly is suspended between the first guide roller and the second guide roller;
   imparting a first line of weakness into the first surface of the belt assembly using a first laser beam, wherein the first laser beam acts on the unsupported portion of the belt assembly between the first guide roller and the second guide roller;
   imparting a second line of weakness into the second surface of the belt assembly using a second laser beam, wherein the second laser beam acts on the unsupported portion of the belt assembly between the first guide roller and the second guide roller;
   wherein the first line of weakness is coincident with the second line of weakness.

24. The method of claim 23, wherein the belt assembly comprises one or more elastic strands disposed between the first substrate and the second substrate.

25. The method of claim 24, further comprising the steps of:
   disposing the belt assembly on an outer circumferential surface of a process member;
   rotating the process member about a longitudinal axis of rotation;
   advancing the belt assembly to a cutting member, wherein the cutting member severs a portion of the one or more elastic strands forming a gap in the one or more elastic strands; and
   advancing the belt assembly to a trim removal member, wherein the trim removal member separates the line of weakness forming a trim portion and a separation edge.

26. The method of claim 25, further comprising: advancing a discrete component toward the process member; orienting the discrete component; and positioning the discrete component on a portion of the belt assembly.

27. The method of claim 26, further comprising the step of advancing the separation edge of the belt assembly through a nip formed by a first roller and a second roller, wherein the first roller and the second roller strain the separation edge of the belt assembly.

28. The method of claim 23, wherein at least one of a first circumferential surface of the first guide roller and a second outer circumferential surface of the second guide roller comprises one or more grooves.

29. The method of claim 23, wherein the first laser beam is emitted by a first laser source and the second laser beam is emitted by a second laser source, wherein the first laser source and the second laser source are operated below a cutting power.

30. The method of claim 23, further comprising the step of applying an adhesive to a portion of the belt assembly.

31. The method of claim 25, further comprising the step of activating the separation edge.

32. The method of claim 23, wherein the second surface of the belt assembly is disposed on an outer circumferential surface of the first guide roller and the first surface of the belt assembly is disposed on an outer circumferential surface of the second guide roller.

33. The method of claim 23, wherein the second surface of the belt assembly is disposed on an outer circumferential surface of the first guide roller and an outer circumferential surface of the second guide roller.

34. The method of claim 23, wherein the first surface of the belt assembly is disposed on an outer circumferential surface of the first guide roller and an outer circumferential surface of the second guide roller.

\* \* \* \* \*